(12) United States Patent
Barr et al.

(10) Patent No.: US 7,763,596 B2
(45) Date of Patent: Jul. 27, 2010

(54) SELECTIVE GLUCOCORTICOID RECEPTOR AGONISTS

(75) Inventors: Stephen Alexander Barr, Belfast (GB); Michael Anthony McKervey, Belfast (GB); Hughes Jean-Pierre Miel, Belfast (GB); David William Ray, Belfast (GB); Andrew Michael Brass, Machester (GB)

(73) Assignee: The University of Manchester, Manchester (GB)

(*) Notice: Subject to any disclaimer, the term of this patent is extended or adjusted under 35 U.S.C. 154(b) by 54 days.

(21) Appl. No.: 11/737,185

(22) Filed: Apr. 19, 2007

(65) Prior Publication Data

US 2008/0090792 A1 Apr. 17, 2008

Related U.S. Application Data

(63) Continuation of application No. 10/415,711, filed as application No. PCT/GB01/04888 on Nov. 2, 2001, now abandoned.

(30) Foreign Application Priority Data

| Nov. 3, 2000 | (GB) | .............................. 0026947.2 |
| Jun. 20, 2001 | (GB) | .............................. 00115161.2 |

(51) Int. Cl.
*A61K 31/675* (2006.01)
*A61K 31/56* (2006.01)

(52) U.S. Cl. ........................................ 514/94; 514/182
(58) Field of Classification Search .................... 514/94
See application file for complete search history.

(56) References Cited

U.S. PATENT DOCUMENTS

| 4,226,862 | A | 10/1980 | Riva et al. |
| 4,996,335 | A | 2/1991 | Bodor |
| 5,767,113 | A | 6/1998 | Cohn et al. |
| 5,965,434 | A | 10/1999 | Wolff et al. |
| 6,024,957 | A | 2/2000 | Lazarovits et al. |
| 6,239,124 | B1 | 5/2001 | Zenke et al. |
| 6,753,329 | B2 | 6/2004 | Bockovich et al. |

FOREIGN PATENT DOCUMENTS

| EP | 0 783 001 A | 7/1997 |
| EP | 0783001 | 7/1997 |
| WO | 97/42214 | 11/1997 |
| WO | WO 9742214 A | 11/1997 |
| WO | 00/58523 | 10/2000 |
| WO | WO 00 58523 A | 10/2000 |

OTHER PUBLICATIONS

Meyer: "Differential Effects of Agonists and Antagonists on Autoregulation of Glucocorticoid Receptors in a Rat colonic Adenocarcinoma Cell Line"; Journal of Steroid Biochemistry and Molecular Biology; vol. 62, No. 1, 1997; pp. 97-105 XP001009699.

Rousseau et al.: "Glucocorticoid agonist and antagonist activity of 17,21-acetonide steroids"; Journal of Steroid Biochemisty; vol. 18, No. 3, 1983; pp. 237-244; XP000917808.
Pallardy, et al., "Apoptosis induced by glucocorticoids on lymphocytes: between physiology and pharmacology", C.R. Soc. Biol., 1998, 192, pp. 1051-1063.
Cato, et al., "Mollecular mechanisms of anti-inflammatory action of glucocorticoids", Bio Essays vol. 18, No. 5, 1996, pp. 371-378.
McColl, et al., "Apoptosis induction by the glucocorticoid hormone dexamethasone and the calsium-ATPase inhibitor thapsigargin involves Bcl-2 regulated caspase activation", Molecular and Cellular Endocrinology, vol. 139, 1998, pp. 229-238.
Miyashita, et al., "Investigation of glucocorticoid-induced apoptotic pathway: Processing of Caspase-6 but not Caspase-3", Cell Death and Differentiation, vol. 5, 1998, pp. 1034-1041.
Reichardt, et al., "DNA Binding of the Glucocorticoid Receptor Is Not Essential for Survival", Cell, vol. 93, May 15, 1998, pp. 531-541.
Ray, et al., "Elevated Levels of Adrenocorticotropin (ACTH) Precursors in Post-Adrenalectomy Cushing's Disease and Their Regulation By Glucocorticoids", Journal of Clinical Endocrinology and Metabolism, vol. 80, No. 8, pp. 2430-2436.
Ray, et al., "Glucocorticoid Receptor Structure and Function in Glucocorticoid-resistant Small Cell Lung Carcinoma Cells", Cancer Research vol. 56, Jul. 15, 1996, pp. 3276-3280.
Ray, et al., "Structure/Function of the Human Glucocorticoid Receptor: Tyrosine 735 Is Important for Transactivation", Molecular Endocrinology, vol. 3, No. 11, 1999, pp. 1855-1863.
Riccardi, et al., "Glucocorticoid hormones in the regulation of cell death", Théapie vol. 55, 2000, pp. 165-169.
Cifone, et al., "Dexamethasone-Induced Thymocyte Apopstosis: Apoptotic Signal Involves the Sequential Activation of Phosphoinositide-Specific Phospholipase C, Acidic Sphingomyelinase, and Caspases", Blood vol. 93, No. 7, Apr. 1, 1999, pp. 2282-2296.
Meßmer, et al., "Glucocorticoids potently block tumour necrosis factor-α- and lipopolysaccharide-induced apoptotic cell death in bovine glomerular endothelial cells upstream of caspase 3 activation", British Journal of Pharmacology vol. 127, 1999, pp. 1633-1640.

(Continued)

*Primary Examiner*—Michael G Hartley
*Assistant Examiner*—Melissa Perreira
(74) *Attorney, Agent, or Firm*—Banner & Witcoff, Ltd.

(57) ABSTRACT

This invention is directed to a method for treating an inflammatory condition, treating haematological and other malignancies, causing immunosuppression, or preventing or treating transplant rejection in man or other animals which comprises administering to a patient a compound that has the structure of Formula (I) or Formula (II) as defined below, or a pharmaceutically acceptable derivative thereof or pro-drug therefor, wherein $R=NH_2$, $NHR^1$, $NHOR^2$, $NHNHR^2$, $NHCOR^2$, and $R^1=C_{(1-4)}$alkyl, $C_{(3-6)}$cycloalkyl, $C_n$, where n=1-3, $R_2$=methyl, ethyl, $R_3$=alkyl, cycloalkyl, substituted alkyl, substituted cycloalkyl, aryl, heteroaryl, substituted aryl, or substituted hetrecoaryl; wherein $R^4$, $R^5=C_{(1-4)}$alkyl. Novel compounds according to Formula (III), wherein $R^6$ and $R^7$ are any of H, $CH_3CO$, $CH_3CH_2CO$, $CH_3CH_2CH_2CO$ provided that $R^6$ and $R^7$ are not both H, or Formula (IV), wherein $R^8$ and $R^9$ are any of H, $CH_3CO$, $CH_3CH_2CO$ or $CH_3CH_2CH_2CO$, having use in such methods, are also described.

4 Claims, 25 Drawing Sheets

OTHER PUBLICATIONS

Schmidt, et al., "Glucocorticoids Induce Apoptosis in Human Monocytes: Potential Role of IL-1β", The Journal of Immunology, 1999, pp. 3484-3490.

Yang, et al., "Thymocyte Apoptosis", Journal of Clinical Immunology vol. 19, No. 6, 1999, pp. 337-349.

Ashwell, et al., "Cross-Talk between the T Cell Antigen Receptor and the Gluocorticoid Receptor Regulates Thymocyte Development", Stem Cells, 1996, pp. 490-500.

Brannigan, et al., "Neutrophil Apoptosis Is Delayed in Patients With Inflammatory Bowel Disease", Shock vol. 13, No. 5, 2000, pp. 361-366.

Horwitz, et al., "Nuclear Receptor Coactivators and Corepressors", Molecular Endocrinology vol. 10, No. 10, 1996, pp. 1167-1177.

Perlmann, et al., "Nuclear Receptors in Sicily: All in the Famiglia", Cell vol. 90, Aug. 8, 1997, pp. 391-397.

Evans, et al., "Cooperative and Positional Independent *trans*-Activation Domains of the Human Glucocorticoid Receptor", Cold Spring Harbor Symposia on Quantitative Biology vol. LIII, 1988, pp. 813-818.

Kamei, et al., "A CBP Integrator Complex Mediates Transciptional Activation and AP-1 Inhibition by Nuclear Receptors", Cell vol. 85, May 3, 1996, pp. 403-414.

Hong, et al., "An Additional Region of Coactivator GRIP1 Required for Interaction with the Hormone-binding Domains of a Subset of Nuclear Receptors", The Journal of Biological Chemistry vol. 274, No. 6, Feb. 5, 1999, pp. 3496-3502.

Chen, et al., "Nuclear Receptor Coactivator ACTR Is a Novel Histone Acetyltransferase and Forms a Multimeric Activation Complex with P/CAF and CBP/p300", Cell vol. 90, Aug. 8, 1997, pp. 569-580.

Chen, et al., "A transcriptual co-repressor that interacts with nuclear hormone receptors", Nature vol. 377, Oct. 5, 1998, pp. 454-457.

Schüle, et al., "Functional Antagonism between Oncoprotein c-Jun and Steroid Hormone Receptors", Cold Spring Harbor Symposia on Quantitative Biology vol. LVI, 1991, pp. 119-127.

Miner, et al., "Regulatory crosstalk at composite response elements", TIBS 16, Nov. 1991, pp. 423-426.

Heck, et al., "A distinct modulating domain in glucocorticoid receptor monomers in the repression of activity of the transcription factor AP-1", The EMBO Journal vol. 13, No. 17, 1994, pp. 4087-4095.

Wade, et al., "Glucocorticoid receptor-activator protein-I interactions in drug design", Biochemical Society Transactions vol. 23, 1995, pp. 946-952.

König, et al., "Interference between pathway-specific transcription factors: glucocorticoids antagonize phorbol ester-induced AP-1 activity without altering AP-1 site occupation in vivo" The EMBO Journal vol. 11, No. 6, 1992, pp. 2241-2246.

Caldenhoven, et al., "Negative Cross-Talk between RelA and the Glucocorticoid Receptor: A Possible Mechanism for the Antiinflammatory Action of Glucocorticoids", Molecular Endocrinology vol. 9, No. 4, 1995, pp. 401-412.

Ray, et al., "Physical association and functional antagonism between the p65 subunit of transcription factor NF-κB and the glucocorticoid receptor", Proc. Natl. Acad. Sci. USA vol. 91, Jan. 1994, pp. 752-756.

Scheinman, et al., "Role of Transcriptional Activation of IκBα in Mediation of Immunosuppression by Glucocorticoids", Science vol. 270, Oct. 13, 1995, pp. 283-286.

Scheinman, et al., "Characterization of Mechanisms Involved in Transrepression of NF-κB by Activated Glucocorticoid Receptors", Molecular and Cellular Biology vol. 15, No. 2, Feb. 1995, pp. 943-953.

Heck, et al., "IκBα-independent downregulation of NF-κB activity by glucocorticoid receptor", The EMBO Journal vol. 16, No. 15, 1997, pp. 4698-4707.

Jonat, et al., "Antitumor Promotion and Antiinflammation: Down-Modulation of AP-1 (Fos/Jun) Activity by Glucocorticoid Hormone", Cell vol. 62, Sep. 21, 1990, pp. 1189-1204.

Sher, et al., "Steroid-resistant Asthma: Cellular Mechanisms Contributing to Inadequate Response to Glucocorticoid Therapy", Journal of Clinical Investigation vol. 93, Jan. 1994, pp. 33-39.

Barnes, "Anti-inflammatory actions of glucocorticoids: molecular mechanisms", Clinical Science vol. 94, 1998, pp. 557-572.

Vayssière, et al., "Synthetic Glucocorticoids That Dissociate Transactivation and AP-1 Transrepression Exhibit Antiinflammatory Activity in Vivo", Molecular Endocrinology vol. 11, No. 9, 1997, pp. 1245-1255.

Berghe, et al., "Dissociated Glucocorticoids with Anti-Inflammatory Potential Repress Interleukin-6 Gene Expression by a Nuclear Factor-κB-Dependent Mechanism", Molecular Pharmacology vol. 56, 1999, pp. 797-806.

Hofmann, et al., "Various glucocorticoids differ in their ability to induce gene expression, apoptosis and to repress NF-κB-dependent transcription", FEBS Letters vol. 441, 1998, pp. 441-446.

Wurtz, et al., "A canonical structure for the ligand-binding domain of nuclear receptors", Nature Structural Biology vol. 3, No. 1, Jan. 1996, pp. 87-94.

Sippl, "Boltzmann's principle, knowledge-based mean fields and protein folding. An approach to the computational determination of protein structures", Journal of Computer-Aided Molecular Design vol. 7, 1993, pp. 473-501.

Belvisi, et al., "New Glucocorticosteroids with an Improved Therapeutic Ratio?", Pulmonary Pharmacology & Therapeutics vol. 14, 2001, pp. 221-227.

Belvisi, et al., "Therapeutic Benefit of a Dissociated Glucocorticoid and the Relevance of in Vitro Separation of Transrepression from Transactivation Activity", The Journal of Immunology, 2001, pp. 1975-1982.

Liu, et al., "Hepatocyte Toll-Like Receptor 2 Expression In Vivo and In Vitro: Role of Cytokines In Induction of Rat TLR2 Gene Expression by Lipopolysaccharide", Shock vol. 14, No. 3, 2000, pp. 361-365.

Rousseau, et al., "17β-Carboxamide steroids are a new class of glucocorticoid antagonists", Nature vol. 279, May 10, 1979, pp. 158-160.

The Merck Index (11th edition) AN 2922, 1989, pp. 463-464.

Ashwell et al.; "Cross-Talk between the T Cell Antigen Receptor and the Glucocorticoid Receptor Regulates Thymocyte Development", Stem Cells, vol. 14, p. 490-500, 1996.

Barnes; "Anti-inflammatory actions of glucocorticoids: molecular mechanisms", Clinical Science, vol. 94 p. 557-572, 1998.

Belvisi et al.; "Therapeutic Benefit of a Dissociated Glucocorticoid and the Relevance of In Vitro Separation of Transrepression from Transactivation Activity", Journal of Immunology, p. 1975-1982, 2001.

Belvisi et al.; "New Glucocorticosteroids with an Improved Therapeutic Ratio?", Pulmonary Pharacology & Therapeutics, vol. 14, p. 221-227, 2001.

Berghe et al.; "Dissociated Glucocorticoids with Anti-Inflammatory Potential Repress Interleukin-6 Gene Expression by a Nuclear Factor-κB-Dependent Mechanism", Molecular Pharmacology, vol. 56, p. 797-806, 1999.

Brannigan et al.; "Netrophil Apoptosis is Delayed in Patients with Inflammatory Bowel Disease", Shock, vol. 13, No. 5, p. 361-366, 2000.

Caldenhoven et al.; "Negative Cross-Talk between RelA and the Glucocorticoid Receptor: A Possible Mechanism for the Antiinflammatory Action of Glucocorticoids", Molecular Endocrinology, vol. 9, No. 5, p. 401-412, 1995.

Cato et al.; "Molecular mechanisms of anti-inflammatory action of glucocorticoids", BioEssays, vol. 18, No. 5, p. 371-378, 1996.

Chen et al.; "Nuclear Receptor Coactivator ACTR Is a Novel Histone Acetyltransferase and Forms a Multimeric Activation Complex with P/CAF and CBP/p300", Cell, vol. 90, p. 569-580, Aug. 8, 1997.

Chen et al.; "A transcriptional co-repressor that interacts with nuclear hormone receptors", Nature, vol. 377, p. 454-457, Oct. 5, 1995.

Cifone et al.; "Dexamethasone-Induced Thymocyte Apoptosis: Apoptotic Signal Involves the Sequential Activation of Phosphoinositide-Specific Phospholipase C, Acidic Sphingomyelinase, and Caspases", Blood, vol. 93, No. 7, p. 2282-2296, Apr. 1, 1999.

Evans et al.; Cooperative and Positional Independent trans-Activation Domains of the Human Glucocorticoid Receptor, Cold Spring Harbor Symposia on Quantitative Biology, vol. LIII, p. 813-818, 1988.

Heck et al.; "A distinct modulating domain in glucocorticoid receptor monomers in the repression of activity of the transcription facto AP-1", The EMBO Journal, vol. 13, No. 17, p. 4087-4095, 1994.

Heck et al.; "IκBα-independent downregulation of NF-κB activity by glucocorticoid receptor", The EMBO Journal, vol. 16, No. 15, p. 4698-4707, 1997.

Hofmann et al.; "Various glucocorticoids differ in their ability to induce gene expression, apoptosis and to repress NF-κB-dependent transcription", FEBS Letters, vol. 441, p. 441-446, 1998.

Hong et al.;"An Additional Region of Coactivator GRIP1 Required for Interaction with the Hormone-binding Domains of a Subset of Nuclear Receptors", The Journal of Biological Chemistry, vol. 274, No. 6, p. 3496-3502, Feb. 5, 1999.

Horwitz et al.; "Nuclear Receptor Coactivators and Corepressors", Molecular Endocrinology, p. 1167-1177, 1996.

Jonat et al.; "Antitumor Promotion and Antiinflammation: Down-Modulation of AP-1 (Fos/Jun) Acitivity by Glucocorticoid Hormone", Cell, vol. 62, p. 1189-1204, Sep. 21, 1990.

Kam et al.; "Combination IL-2 and IL-4 Reduces Glucocorticoid Receptor-Binding Affinity and T Cell Response to Glucocorticoids", The Journal of Immunology, vol. 151, No. 7, p. 3460-3466, Oct. 1, 1993.

Kamei et al.; "A CBP Integrator Complex Mediates Transcriptional Activation and AP-1 Inhibition by Nuclear Receptors", Cell, vol. 85, p. 403-414, May 3, 1996.

König et al.; "Interference between pathway-specific transcription factors: glucocorticoids antagonize phorbol ester-induced AP-1 activity without altering AP-1 site occupation in vivi", The EMBO Journal, vol. II, No. 6, p. 2241-2246, 1992.

Lefebvre et al.; "Improvement in Glucocorticoid Receptor Binding Affinity Concomitant to Shift from Antagonist to Agonist Activity in a Series of 17β-Carboxamide Derivatives of Dexamethasone" J. Steroid Biochem., vol. 33, No. 4A, , p. 557-563, 1989.

Liu et al.; "Hepatocyte Toll-like Receptor 2 Expression in Vivio and in Vitro: Role of Cytokines in Induction of Rat TLR2 Gene Expression by Lipopolysaccharide", Shock, vol. 14, No. 3, p. 361-365, 2000.

McColl et al.; "Apoptosis induction by the glucocorticoid hormone dexamethasone and the calcium-ATPase inhibitor thapsigargin involves Bcl-2 regulated caspase acitivation", Molecular and Cellular Endocrinology, p. 229-238, 1998.

Meβmer et al.; "Glucocorticoids potently block tumour necrosis factor-α- and lipopolysaccharide-induced apoptotic cell death in bovine glomerular endothelial cells upstream of caspase 3 activation", British Journal of Pharacology, vol. 127, p. 1633-1640, 1999.

Meyer et al.; "Differential Effects of Agonists and Antagonists on Autoregulation of Glucocorticoid Receptors in a Rat Colonic Adenocarcinaoma Cell Line", J. Steroid Biochem. Molec. Biol., vol. 69, No. 1, p. 97-105, 1997.

Miner et al.; "Regulatory crosstalk at composite response elements", TIBS, vol. 15, p. 423-426, Nov. 1991.

Miyashita et al.; "Investigation of glucocorticoid-induced apoptotic pathway: Processing of Caspase-6 but not Caspase-3", Cell Death and Differentiation, vol. 5, p. 1034-1041, 1998.

Pallardy et al.; "Apoptosis induced by glucocorticoids on lymphocytes: between physiology and pharmacology", C.R. Soc. Biol., vol. 192, p. 1051-1063, 1998.

Perlman et al.; "Nuclear Receptors in Sicily: All in the Famiglia", Cell, vol. 90, p. 391-397, Aug. 8, 1997.

Ray et al.; "Physical association and functional antagonism between the p65 subunit of transcription factor NF-κB and the glucocorticoid receptor", Proc. Natl. Acad. Sci., vol. 91, 752-756, Jan. 1994.

Ray et al.; "Elevated Levels of Adrenocorticotropin (ACTH) Precursors in Post-Adrenalectomy Cushing's Disease and Their Regulation by Glucocorticoids", J C E & M, vol. 80, No. 8, p. 2430-2436, 1995.

Ray et al.; "Glucocorticoid Receptor Structure and Function in Glucocorticoid-resistant Small Cell Lung Carcinoma Cells", Cancer Research, vol. 56, p. 3276-3280, Jul. 15, 1966.

Reichardt et al.; "DNA Binding of the Glulcocorticoid Receptor Is Not Essential for Survival", Cell, vol. 93, p. 531-541, May 15, 1998.

Riccardi et al.; "Glucocorticoid hormones in the regulation of cell death", Therapie, vol. 55, p. 165-169. 2000.

Rosseau et al.; "17β-Carboxamide steroids are a new class of glucocorticoid antagonists", Nature, vol. 279, p. 158-160, May 10, 1979.

Rosseau et al.; "Glucocorticoid Agonist and Antagonist Activity of 17, 21-Acetonide Steroids", Journal Steroid Biochem. vol. 18, No. 3, p. 237-244, 1983.

Scheinmann et al.; "Characterization of Mechanisms Involved in Transrepression of NK-κB by Activated Glucocorticoid Receptors", Moleculare and Cellular Biology, vol. 15, No. 2, p. 943-953, Feb. 1995.

Scheinmann et al.; "Role of Transcriptional Activation of IκBα in Meditation of Immunosuppression by Glucocorticoids", Science, vol. 270, p. 283-286, Oct. 13, 1995.

Schmidt et al.; "Glucocorticoids Induce Apoptosis in Human Monocytes: Potential Role of IL-1β", Journal of Immunology, vol. LVI, p. 3484-3490, 1999.

Schüle et al.; "Functional Antagonism between Oncoprotein c-Jun and Steroid Hormone Receptors", Cold Spring Harbour Symposium and Qualitative Biology, vol. 93, p. 119-127, 1991.

Sher et al.; "Steroid-resistant Asthma (Cellular Mechanisms Contributing to Inadequate Response to Glucocorticoid Therapy)" J. Clin. Invest., vol. 93, p. 33-39, Jan. 1994.

Sippl; "Boltzmann's principle, knowledge-based mean fields and protein folding. An approach to the computational determination of protein structures", Journal of Computer-Aided Molecular Design, vol. 7, p. 473-501, 1993.

Suzuki et al.; "Modulation of Neutrophil Apoptosis in Plasma of Patients after Orthognathic Surgery", Journal of Surgical Research, vol. 130, p. 100-118, 2006.

The Merk Index, 11th Edition, p. 436-464m 1989.

Tran et al.; "Absence of *Porphyromonas asaccharolytica, Bacteroides fragilis* and *Chlamydia pnueumoniae* in human subgingival plaque", Oral Micorbiol. Immunol., vol. 12, p. 377-378, 1997.

Vayssière et al.; "Synthetic Glucocorticoids That Dissociate Transactivation and AP-1 Transrepression Exhibit Antiinflammatory Activity in Vivo", Molecular Endocrinology, vol. 11, No. 9, p. 1245-1255, 1997.

Wade et al.; "Glucocorticoid receptor-acitvator protein-I interactions in drug design", Biochemical Society Transactions, vol. 23, p. 946-652, 1995.

Wurtz et al.; "A canonical structure for the ligand-binding domain of nuclear receptors", Nature Structural Biology, vol. 3, No. 1, p. 87-94, Jan. 1996.

Yand et al.; "Thymocyte Apoptosis", Journal of Clinical Immunology, vol. 19, No. 6, p. 337-349, 1999.

Dexamethasone

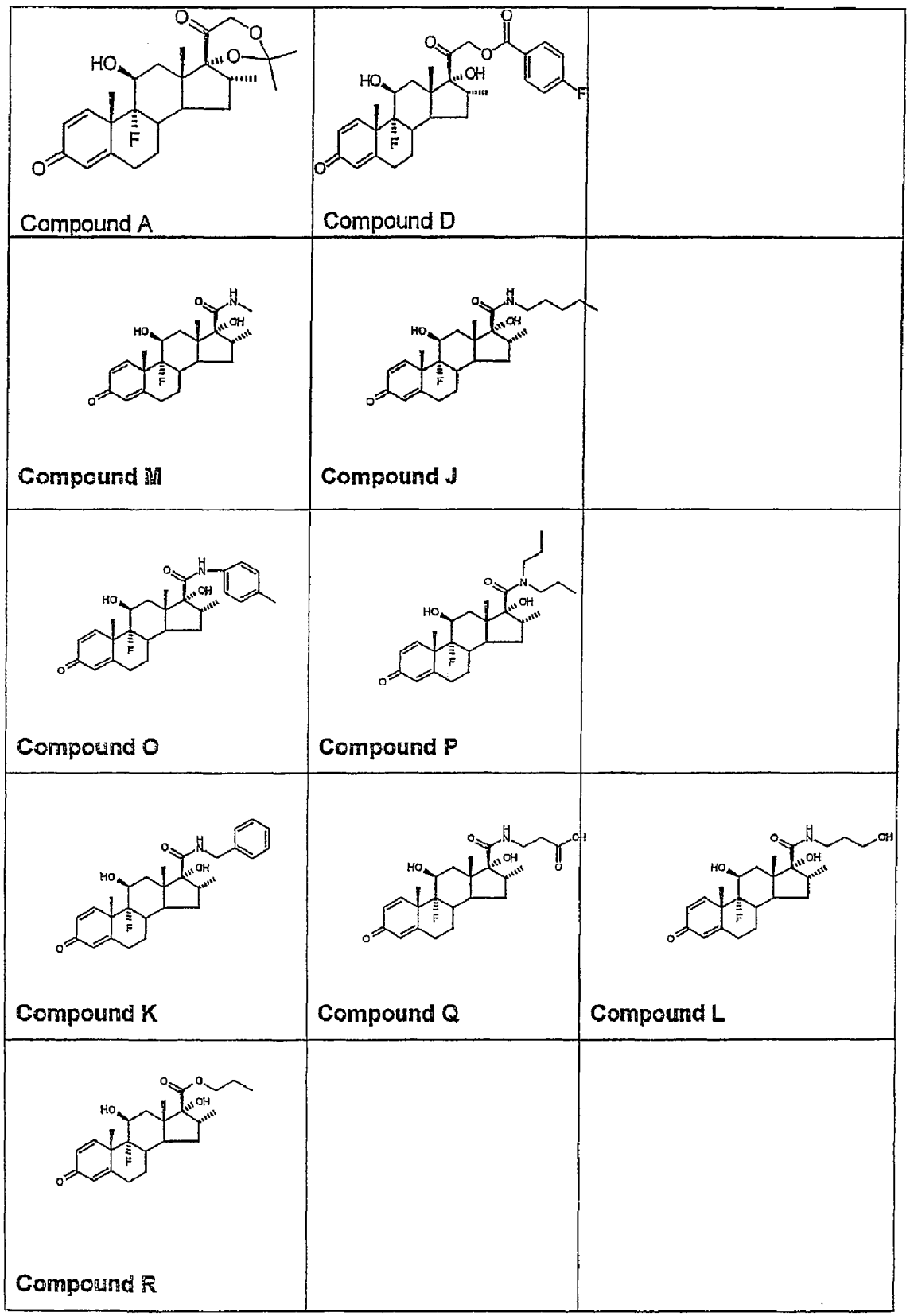
Figure 2A Compounds A, D and G to T

Figure 2A continued
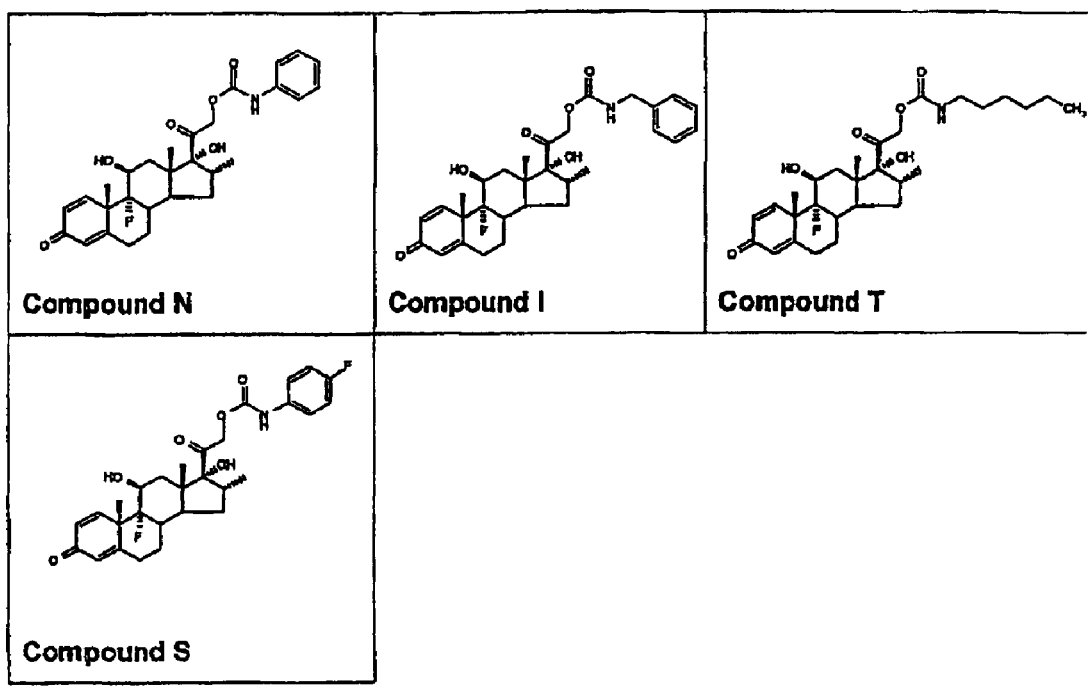
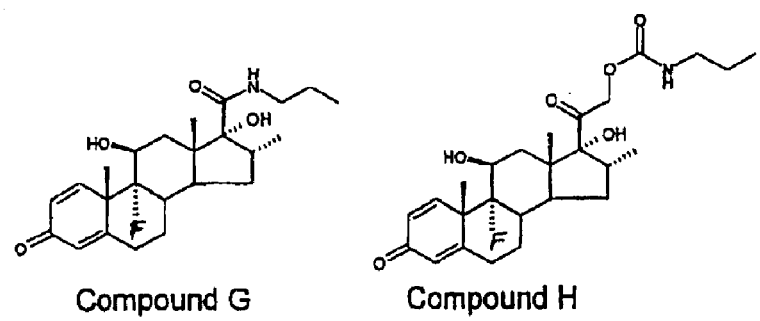

Compounds

Figure 4

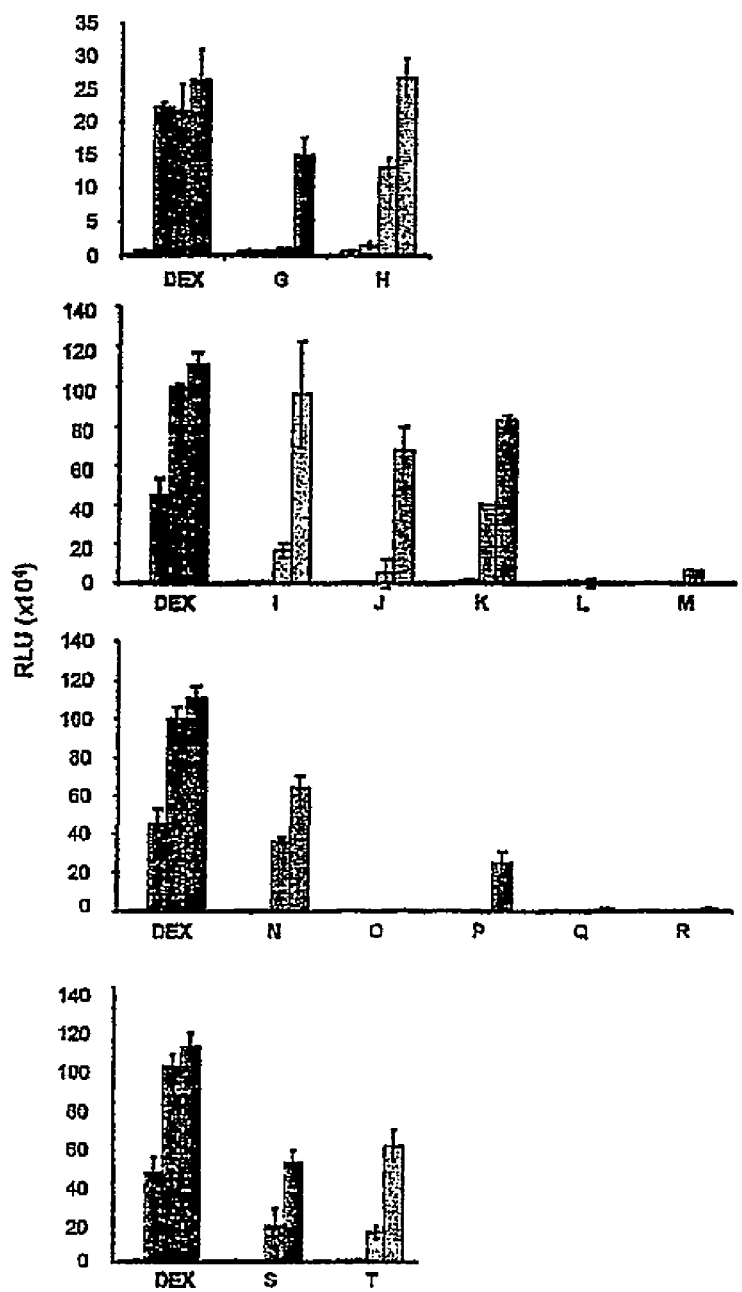

Transactivation at 0,1,10,100nM. The pcDNA3-GR expression vector was transfected along with the AH3-luc reporter gene in COS 7 cells as described, and were divided into treatment and control groups. The cells were incubated with 0,1,10 or 100nM steroid for 18 before harvest and luciferase and assay. Bars indicate the mean and standard deviation (n=3). Experiment performed on three occasions with similar results.

Figure 5

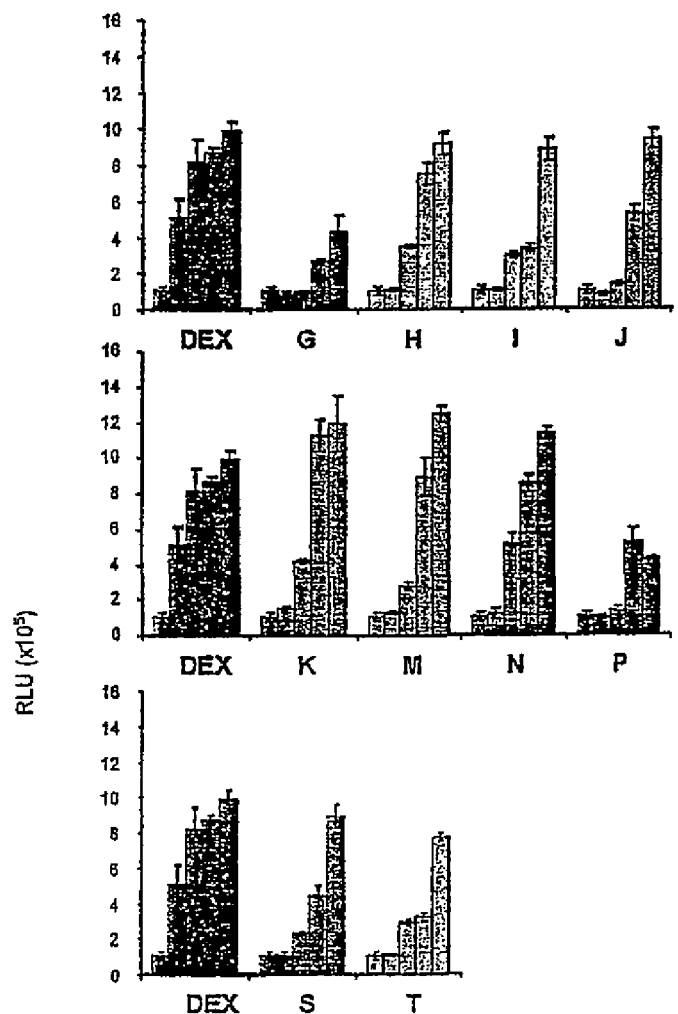

Transactivation at 0,1,10,100, 500nM. The pcDNA3-GR expression vector was transfected along with the AH3-luc reporter gene in COS 7 cells as described, and were divided into treatment and control groups. The cells were incubated with 0,1,10,100 or 500nM steroid for 18 before harvest and luciferase and assay. Bars indicate the mean and standard deviation (n=3). Experiment performed on three occasions with similar results.

Figure 7

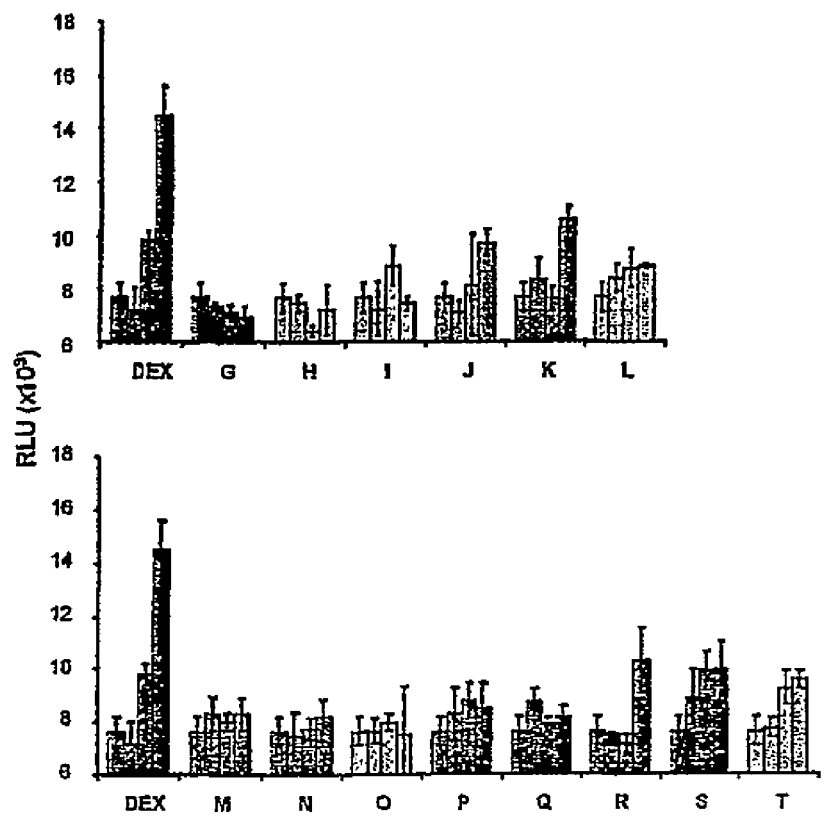

SRC-1 recruitment at 0,1,10,100nM. GR-VP16, Gal4-SRC-1 and the pG5 reporter plasmid constructs were transfected into COS-7 cells. Cells were divided into treatment and control groups (n=3), and were exposed to steroids for 18 hours before harvest and firefly luciferase assays. Results are shown as mean +/- standard error of the mean (sem) of one experiment performed in triplicate, representative of three separate experiments.

Endogenous TAT activity at 100nM Dex or G. HEP G2 cells were incubated for 18 hours with 1μM steroid. Cell protein was prepared by sonication. The TAT assay was then performed on 100μg of total cell protein. Results are shown as mean +/- standard deviation (sd) of one experiment performed in triplicate, representative of three separate experiments.

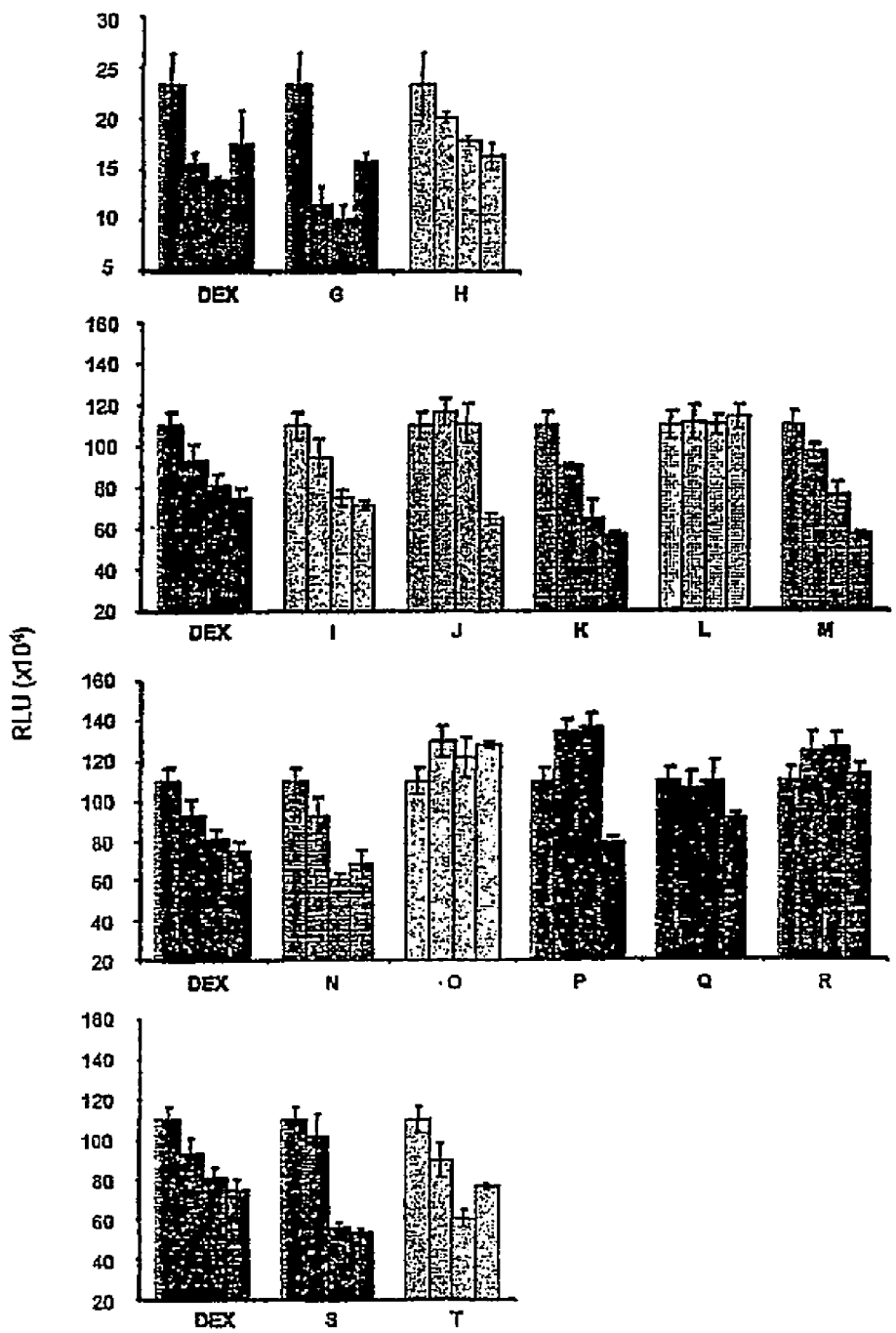

Figure 10

Repression of P65 function at 0,1,10,100nM. COS7 cells were transfected with an NFkB reporter gene (NRE-luc), pcDNA3-GR and P65. Cells were divided post-transfection, and were incubated with the indicated concentrations of steroid. After 18 hours cells were harvested for luciferase reporter gene assay. Results are shown as mean +/- sem of one experiment performed in triplicate, representative of three separate experiments.

Figure 12

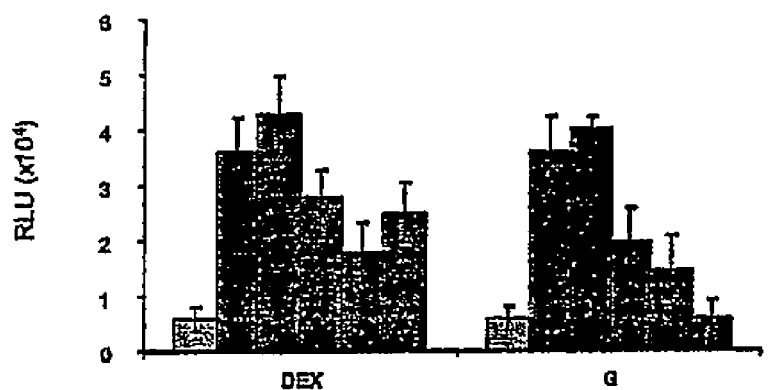

Repression of the TNF activation of A549 cells. A549 cells were transfected with an NFkB reporter gene (NRE-luc). Cells were divided post-transfection, and were incubated with the indicated concentrations of steroid. After 18 hours cells were harvested for luciferase reporter gene assay. Results are shown as mean +/- sem of one experiment performed in triplicate, representative of three separate experiments. Grey = no treatment, green = post TNF, red =1,10,100,500nM DEX, blue=1,10,100,500nM G Repression IL-8 production in A549 cells. A549 cells were treated with 100nM novel steroids. After 18 hours the supernatant was harvested an IL-8 assay. Results are shown as mean +/- sem of one experiment performed in triplicate, representative of three separate experiments.

Nuclear localisation provoked by compounds

Nuclear localisation. COS 7 cells were transfected with GFP-GR, and were treated with 100nM ligand for 1 hour before methanol fixation, and mounting.

Figure 16 Nuclear localization induced by the second series of compounds
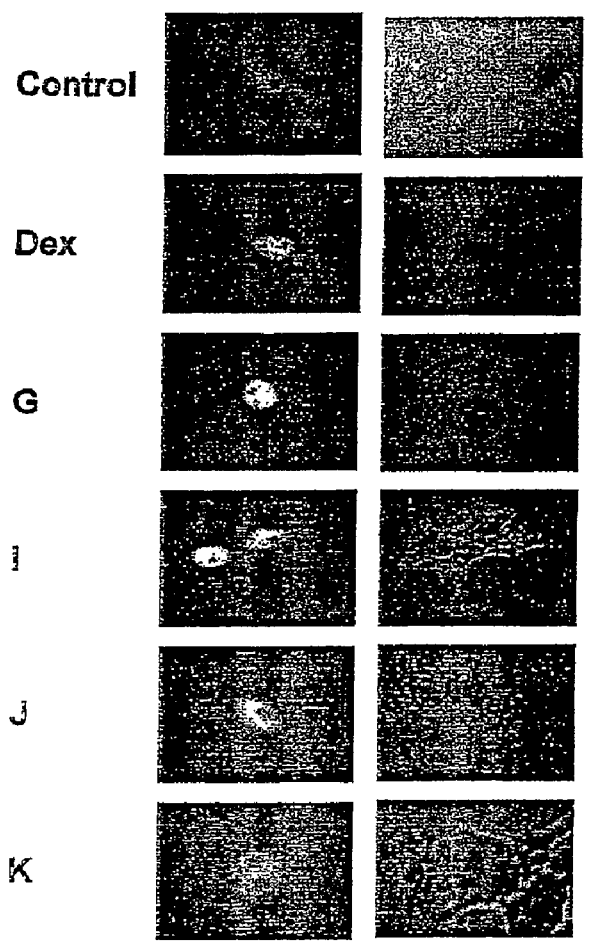
Nuclear localisation. COS 7 cells were transfected with GFP-GR, and were treated with 100nM ligand for 1 hour before methanol fixation, and mounting.

Figure 16 (continued) Nuclear localization induced by the second series of compounds
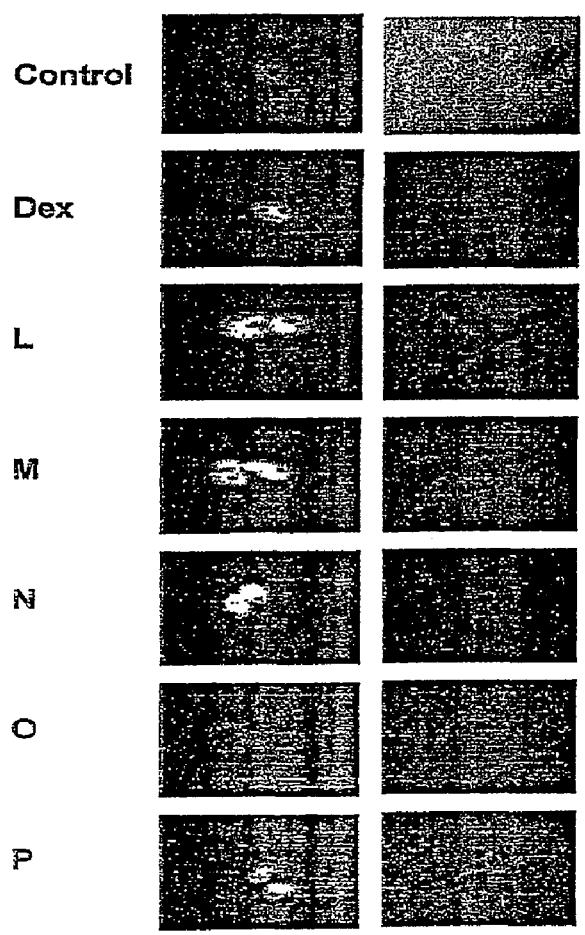
Nuclear localisation. COS 7 cells were transfected with GFP-GR, and were treated with 100nM ligand for 1 hour before methanol fixation, and mounting.

Figure 17

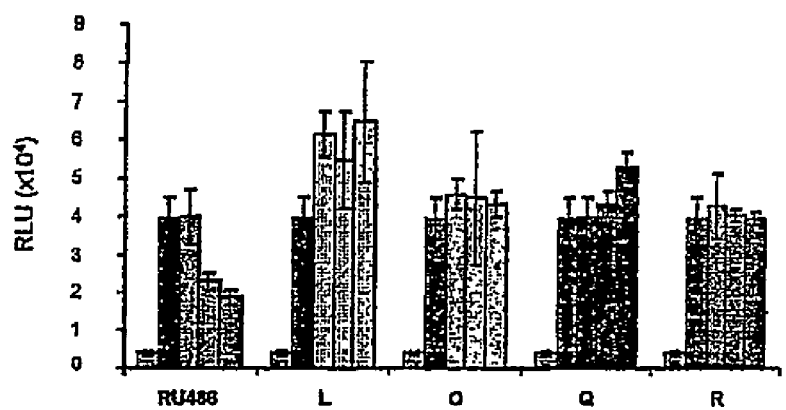

Repression of dexamethasone stimulated transactivation by putative antagonists. The transactivation sensitive AH3 reporter gene construct and the pcDNA3-GR expression vector were transfected into COS 7 cells. Cells were divided and incubated with 1nM Dexamethasone and either 0, 1, 10 or 100nM of RU486, L, O, Q or R 18 hours before harvest and reporter gene assay. Bars indicate the mean and standard deviation (n=3). Experiment performed on three occasions with similar results. Grey = no treatment, red =1nM DEX.

Figure 18

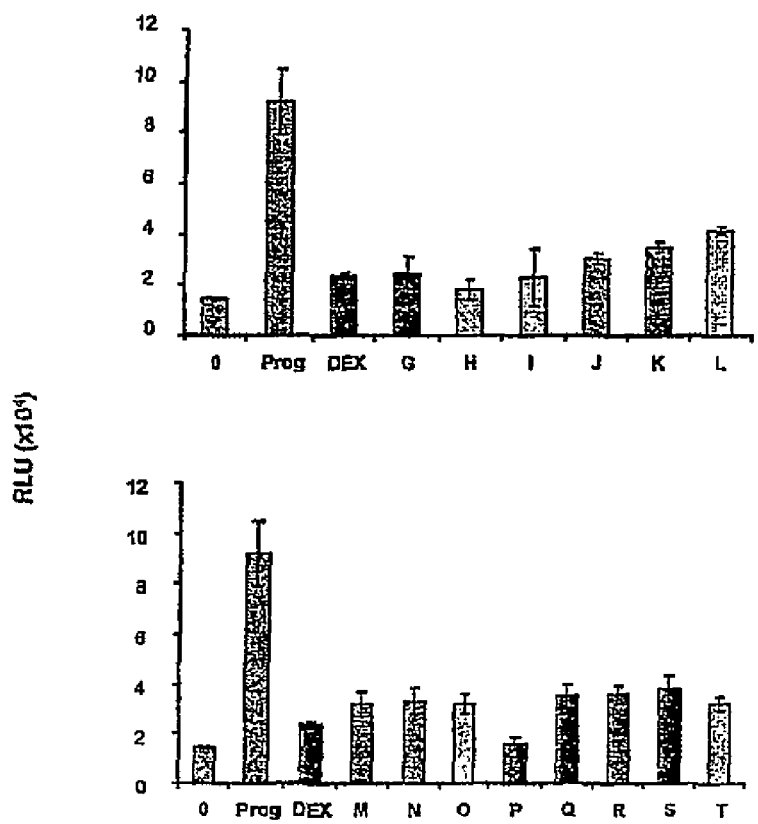

Progestogen activity of the novel steroid compounds. The AH3 reporter gene construct and the pSEO-PRB expression vector were transfected into COS 7 cells. Cells were divided and incubated with 100nM of Progesterone, Dexamethasone or the novel steroids 16 hours before harvest and reporter gene assay. Bars indicate the mean and standard deviation (n=3). Experiment performed on three occasions with similar results.

Figure 19    INHIBTION CURVES
Assay: 232010-1 Glucocorticoid
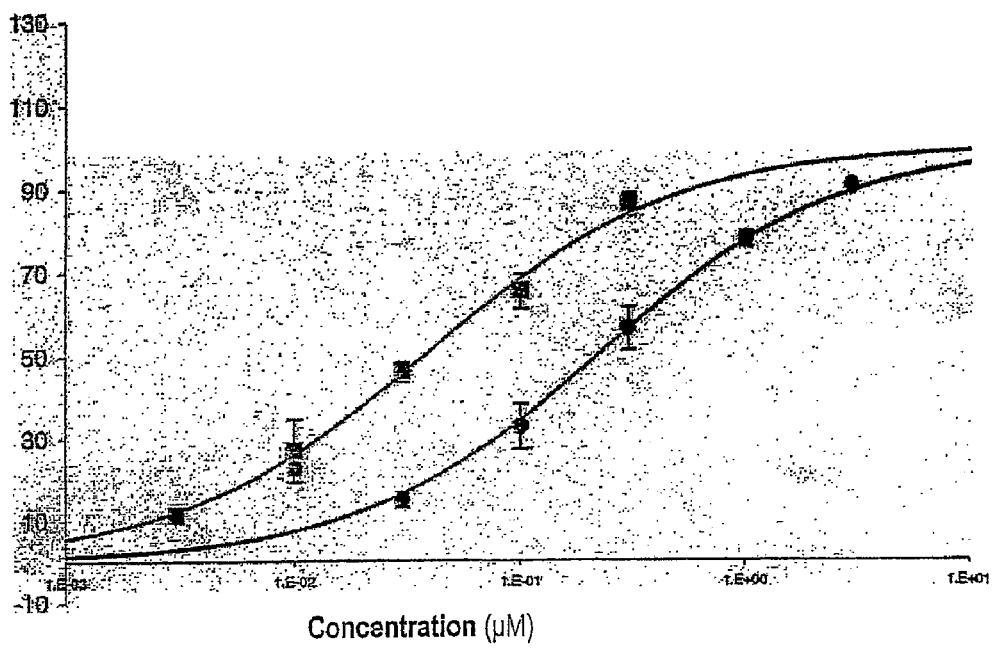
Concentration (µM)
| Compound | IC$_{50}$ | K$_i$ | n$_H$ |
|---|---|---|---|
| ● MAH-1 (1019212) | 0.232 ± 0.049 µM | 0.105 ± 0.022 µM | 0.846 ± 0.051 |
| ■ Dexamethasone | 0.04 ± 0.008 µM | 0.018 ± 0.004 µM | 0.804 ± 0.023 |
MAH-1 (1019212) is Compound G CEM C7A glucocorticoid induced apoptosis. CEM C7A cells were incubated with ligand 100nM for 72 before acridine orange staining and fluorescent microscopy. Total cells, and apoptotic cells were counted.

Apoptosis in CEM C7A cells. CEM C7A cells were treated with 100nM novel steroids. After 72 hours the medium was removed and an MTS assay was performed to measure cell number. Results are shown as mean +/- sem of one experiment performed in triplicate, representative of three separate experiments.

SELECTIVE GLUCOCORTICOID RECEPTOR AGONISTS

FIELD OF THE INVENTION

Glucocorticoids (GCs) have been used therapeutically for many years to treat inflammation, as immunosuppressants and in the treatment of lymphoproliferative disorders and certain other malignancies[1;2]. These compounds are the most potent and effective anti-inflammatory agents known. The use of GCs has been limited by their multiple and often devastating side effects. This invention concerns improvements to GCs such that the therapeutic effects of the selected agonists is maintained but the potential for the compounds to cause harmful side-effects is significantly reduced.

BACKGROUND OF THE INVENTION, AND PRIOR ART

GCs were first introduced into medicine in the 1950's. Early enthusiasm for these drugs, due to success in controlling inflammation in a wide range of diseases, was soon tempered by the realisation that these compounds cause a very wide range of side effects that were often serious, often irreversible and in many cases more serious than the inflammatory condition under treatment.

The diseases in which GCs have been shown to have a pronounced anti-inflammatory effect include inflammatory arthritides such as rheumatoid arthritis, ankylosing spondylitis and psoriatic arthropathy, other rheumatoid diseases such as systemic lupus erythematosis, scleroderma, vasculitides including temporal arteritis and polyarteritis nodosa, inflammatory bowel disease such as Crohns disease and ulcerative colitis, lung diseases such as asthma and chronic obstructive airways disease, as well as many other conditions such as polymyalgia rheumatica. GCs have also been used very extensively for their immunosuppressive properties in the prevention and treatment of transplant rejection. Finally GCs have been used for their anti-tumour effects in a number of malignancies. The activity of GCs is in the treatment of lymphoproliferative and other malignances is thought to be due to the ability of GCs to induce apoptosis[3;4].

The use of GCs, particularly in inflammatory disease, has been severely limited by their side effects that are discussed below. A number of approaches have been taken to overcome the side effects of the drugs. The most frequently adopted approach has been to apply the steroid locally to the site of inflammation. Target organs where this approach has been adopted include the lung with oral inhalation for the treatment of asthma and chronic obstructive airways disease; the nose with local installation for the treatment of allergic rhinitis; the eye with local installation for the treatment of a number of serious inflammatory eye conditions such as uveitis; in large joints with intra-articular injection of steroids to treat inflammation; and on the skin for the treatment of eczema, psoriasis and a range of other conditions of the skin. Local delivery has allowed dose reduction with a consequent reduction in systemic side effects. Systemic side effects have been reduced further by the introduction over recent years of so-called "soft steroids" such as fluticasone for topical application. These soft steroids are inactivated rapidly by metabolism following absorption into the systemic circulation thus minimising systemic side effects. Local application of soft steroids, however, is still associated with significant local side effects such as skin thinning. Soft steroids are of no use when systemic administration of the drug is required in diseases such as temporal arteritis or polymyalgia rheumatica.

The side effects of steroids include the following:

Osteoporosis; growth impairment; avascular osteonecrosis; proximal myopathy; impaired glucose tolerance or frank diabetes; fluid retention and oedema; hypertension; hypokalaemia; Cushingoid faces; weight gain; obesity; euphoria; psychosis; insomnia; raised intracranial pressure; aggravation of epilepsy; memory impairment; hippocampal atrophy; peptic ulceration; pancreatitis; suppression of the hypothalamic pituitary axis; raised introcular pressure; glaucoma; papiloedema; skin thinning; reduced resistance to infection; impaired wound healing.

Despite this catalogue of side effects these drugs are still used very widely because their anti-inflammatory effects exceed those of any other drug class; and they continue to have a central role in the treatment and prevention of transplant rejection and the treatment of lymphoproliferative disorders and certain other malignancies. There is thus a need for novel steroids with the same efficacy as the existing drugs in this class but with a reduced side effect potential.

GCs act via specific glucocorticoid receptors (GR), members of the nuclear receptor superfamily. Hormone binding promotes receptor dimerisation, DNA binding, and transcriptional activation. This mechanism of GC action is well-defined in-vitro, and is critical for regulation of the hypothalamic-pituitary-adrenal axis and gluconeogenesis in-vivo[5-8]. Hormone bound receptor is also able to influence gene transcription in a dimerisation-independent manner by interfering with the activity of transcription factors, such as AP-1 and NFkB, which are critically involved in the inflammatory reaction.

The induction of apoptosis in thymocytes and other cell types is a well-recognised effect of GCs. The mechanism behind GCs induction of apoptosis is unclear, although it is commonly believed to involve transcriptional activation for example the activation of the caspase pathway[9]. This remains controversial[10-13] and one unexpected finding we made, leading to the first aspect of this invention, was the finding that the activities of GCs in terms of their ability to cause activation, their ability to cause repression and their ability to induce apoptosis could be differentiated. Preferred compounds, as will be discussed below, are those that retain the ability to repress gene expression and induce apoptosis but lose the ability to activate gene expression.

The induction of apoptosis in T lymphocytes may be important to the immunosuppressive activity of GCs. In addition this same mechanism may be important in the anti-inflammatory effects of GCs with the deletion of clonogenic memory T cells responsible for the induction of a response to an antigen[14]. Finally, there is evidence that in certain diseases, the inflammatory processes may, at least in part, depend on failure of apoptosis in inflammatory cells. This has been shown to be the case with neutrophils in inflammatory bowel diseases[15].

After ligand binding, the GR migrates from the cytoplasm of the cell to the nucleus, and binds to glucocorticoid response elements in the regulatory region of target genes. The activated GR then recruits co-factors, including the glucocorticoid receptor interacting protein 1 (GRIP-1) and steroid receptor coactivator 1 (SRC1). These accessory proteins bind to the receptor and link the GR with the general transcription machinery[16-22].

Glucocorticoid effects on transcription may be mediated by both the direct binding of activated GR to target DNA, homodimerisation and recruitment of co-activators but also by GR interfering with other transcription factor function, including AP-1, NFkB and NUR77[23-31]. These two modes of receptor activity are dissociable, that is negative effects on NFkB activity retained but with loss of transactivation. It appears that this second mechanism is largely responsible for mediating the therapeutically desirable anti-inflammatory activity of the GR[28;31-33]. Interestingly, the IC50 for inhibition of AP-1 or NFkB (0.04 nM) is lower than the EC50 for activation of target genes (5 nM)[8;34], yet despite that, high doses of GCs are frequently required to treat patients with inflammatory disease. It appears that cytokines expressed at the site of inflammation may induce relative glucocorticoid resistance, possibly by activating AP-1 or NFkB[19;23;31;34-37]. This is of importance as the pro-inflammatory cytokines signal by activation of NFkB, and the majority of the anti-inflammatory actions of GCs are thought to be mediated by opposing NFkB action.

Specific mutations in the GR molecule can give rise to dissociated receptors[25;25], that is molecules with relatively inactive transactivation compared with transrepression, and a number of synthetic ligands have differential activity on these two GR pathways, for example RU24858[38]. However, none of the described ligands or molecules has a sufficiently wide dissociation of these two GR actions to be of use therapeutically. In addition RU24858 does not induce apoptosis and hence lacks one of the important activities of GCs, as well as activating the progesterone receptor, thereby having an undesirable lack of specificity of action (unpublished data).

It would be of immense value to identify means to specifically target glucocorticoid action to inhibit NFkB, AP-1 and maintain the ability to induce apoptosis, and at the same time greatly reduce transactivational activity.

Previous studies have tried to differentiate the effects of known and novel steroids in terms of ability to cause transactivation and transrepression[39;40]. To date no new compounds have been developed. We describe a strategy whereby we were able to identify compounds with useful therapeutic activity.

According to a first aspect of the present invention there is provided a method for treating an inflammatory condition, treating haematological and other malignancies, causing immunosuppression or preventing or treating transplant rejection in man or other animals which comprises administering to a patient a compound that has the structure of Formula I or Formula II as defined below, or a pharmaceutically acceptable derivative thereof or pro-drug therefor

FORMULA I

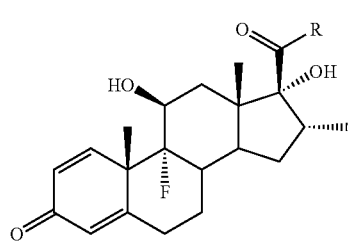

Wherein R=$NH_2$, $NHR^1$, $NHOR^2$, $NHNHR^2$, $NHCOR^2$,

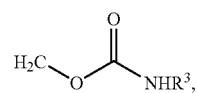

and $R^1$=$C_{(1-4)}$ alkyl, $C_{(3-6)}$cycloalkyl,

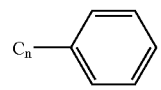

where n=1-3,
$R^2$=methyl, ethyl,
$R^3$=alkyl, cycloalkyl, substituted alkyl, substituted cycloalkyl, aryl, heteroaryl, substituted aryl, or substituted heteroaryl;
OR

FORMULA II

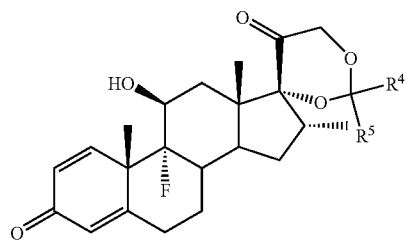

Wherein $R^4,R^5$=$C_{(1-4)}$ alkyl.

The alkyl groups of any of any of $R^1$ to $R^5$ may be straight or branched chain.

In accordance with this method the compounds have been found to induce apoptosis in pro-inflammatory cells.

According to a second aspect of the present invention there is provided a compound according to Formula III or Formula IV defined below:

FORMULA III

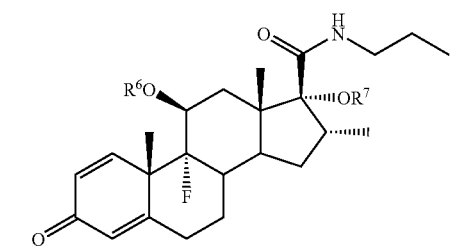

Wherein $R^6$ and $R^7$ are any of H, $CH_3CO$, $CH_3CH_2CO$, $CH_3CH_2CH_2CO$ provided that $R^6$ and $R^7$ are not both H,
OR

FORMULA IV

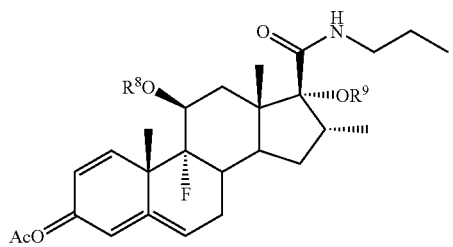

Wherein $R^8$ and $R^9$ are any of H, $CH_3CO$, $CH_3CH_2CO$ or $CH_3CH_2CH_2CO$.

The compounds having the structure of Formula III or IV are useful as pro-drugs. By the term "pro-drug" is meant a compound that undergoes a chemical conversion to become an active drug when metabolised by the body. This normally results in increased drug effectiveness through an increase of absorption by the body, a prolongation of the duration of action in the body or through a reduction of certain side effects.

According to a third aspect of the present invention there is provided a compound according to Formula I or II as defined above, or a pharmaceutically acceptable derivative thereof or pro-drug therefor, or a compound according to Formula III or IV, for use as a medicine. These compounds are particularly effective in the treatment of an inflammatory condition, for treating haematological and other malignancies, causing immunosuppression or the prevention or treatment of transplant rejection.

According to a fourth aspect of the present invention there is provided the use of a compound according to Formula I or II as defined above, or a pharmaceutically acceptable derivative thereof or pro-drug therefor, or a compound according to Formula III or IV, in the manufacture of a medicament for the treatment of an inflammatory condition, for treating haematological and other malignancies, causing immunosuppression or preventing or treating transplant rejection.

According to a fifth aspect of the present invention there is provided a pharmaceutical composition which comprises a compound according to Formula I or II as defined above, or a pharmaceutically acceptable derivative thereof or pro-drug therefor, or a compound according to Formula III or IV, and a pharmaceutically acceptable carrier. Such a composition has particular use in the treatment of an inflammatory condition, for treating haematological and other malignancies, causing immunosuppression or the prevention or treatment of transplant rejection. The sixth aspect of the present invention is directed to the use of such a composition in the manufacture of a medicament for the treatment of an inflammatory condition, for treating haematological and other malignancies, causing immunosuppression or preventing or treating transplant rejection.

According to a seventh aspect of the present invention there is provided a method of inducing apoptosis in target cells, which comprises administering to the target cells or to the vicinity in which the target cells are located a Compound according to Formula I or II as defined above or a pharmaceutically acceptable derivative thereof or pro-drug therefore, or a compound according to Formula III or IV. The eighth aspect of the present invention is directed to the use of compound according to Formula I or II as defined above or a pharmaceutically acceptable derivative thereof or pro-drug therefor, or a compound according to Formula III or IV, in the manufacture of a medicament for inducing apoptosis in target cells. The target cells are generally pro-inflammatory cells or malignant cells. Thus, this aspect of the invention is useful for treating inflammation and to treat haematological and other malignancies.

BRIEF DESCRIPTION OF THE DRAWINGS

FIGS. 2A and 2B illustrate the structures of compounds identified as Compounds A, D, G through T, 2 through 5 and 7.

FIG. 4 also illustrates dose response data of dexamethasone and Compounds G through T in the transactivation (luminescence) assay using artificially expressed glucocorticoid receptor in the COS 7 monkey kidney cell line.

FIG. 5 also illustrates additional dose response data of dexamethasone and Compounds G through K, M, N, P, S and T in the transactivation (luminescence) assay using artificially expressed glucocorticoid receptor in the COS 7 monkey kidney cell line.

FIG. 7 illustrates additional dose response of dexamethasone and Compounds G through T in the SRC-1 association (luminescence) assay by mammalian two-hybrid analysis.

FIG. 10 illustrates additional dose response data for dexamethasone and Compounds G through T in the transrepression assay (luminescence) using artificially expressed glucocorticoid receptor and P65 in the COS 7 monkey kidney cell line.

FIG. 12 illustrates additional dose response data for dexamethasone and Compound G in the transrepression assay (luminescence) using endogenous glucocorticoid receptor in the A549 Lung Epithelial Cell Line.

FIG. 16 illustrates the nuclear translocation associated with dexamethasone, and Compounds G, I through K, and L through P also using GFP tagged glucocorticoid receptor and fluorescent microscopy.

FIG. 17 illustrates assay (luminescence) results of Type II Antagonist Activity of Compounds L, O, Q and R in competition with dexamethasone transactivation (compete with dexamethasone for glucocorticoid receptor binding).

FIG. 18 illustrates the results of a progestogen activity assay using progesterone receptor transactivation as exhibited by Compounds G through T.

FIG. 19 illustrate the results of a ligand binding assay with dexamethasone and Compound G.

DETAILED DESCRIPTION

The preferred compounds of Formula I used according to the invention include those wherein R is $NHR^1$ and $R^1$ is methyl, ethyl, propyl, cyclopropyl, butyl, cyclobutyl or

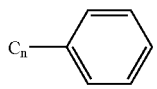

and n=1. Further preferred compounds are those wherein the compound has the structure of formula I where R is

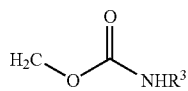

and $R^3$ is straight or branched chain alkyl or substituted alkyl, preferably $C_{(1-6)}$alkyl or substituted alkyl, most preferably propyl or hexyl, or where $R^3$ is a benzyl or a substituted benzyl group, preferably halobenzyl, most preferably fluorobenzyl, or $R^3$ is the substituted alkyl group

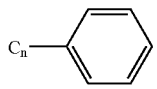

where n=1-6, preferably n=1, or where $R^3$ is a $C_{(3-6)}$ cycloalkyl or substituted cycloalkyl group.

Preferred compounds having a structure according to Formula II include those where $R^4$ and/or $R^5$ is methyl and/or ethyl.

Figure 2B:
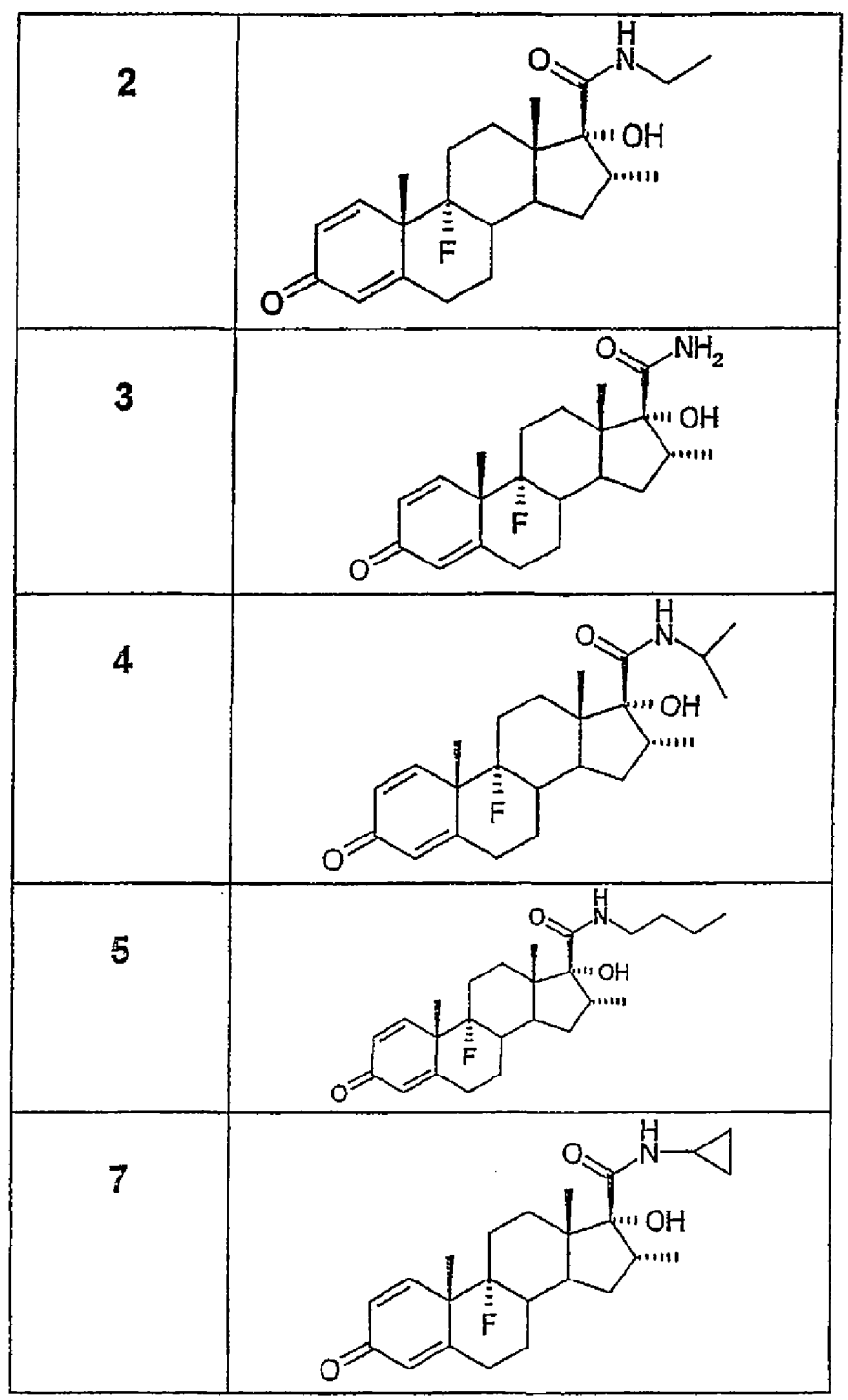

Examples of the particularly preferred compounds used according to the present invention, in addition to the novel compounds of Formula III and IV, are designated as "Compound A", "Compound G" and "Compound H" "Compound I", "Compound K", "Compound M", "Compound N," Compound S", "Compound T", "Compound 2", "Compound 3", "Compound 4", "Compound 5" and "Compound 7", the structures of which are shown in FIGS. 2A and 2B of the accompanying drawings. The most preferred compound used in accordance with the present invention is Compound G in view of its superior potency and selectivity for transrepression over transactivation.

The compositions according to the invention may take a number of different forms depending, in particular on the manner in which the composition is to be used. Thus, for example, the composition may be in the form of a powder, tablet, capsule, liquid, ointment, cream, gel, hydrogel, aerosol, spray, micelle, liposome or any other suitable form that may be administered to a person or animal. It will be appreciated that the vehicle of the composition of the invention should be one which is well tolerated by the subject to whom it is given and enables delivery of the compounds to the target tissue. The compounds used according to this invention may be administered by any route including but not limited to oral inhalation, local installation into the nose or eye, local injection into joints or muscles, orally in the form of capsules, tablets, liquids or suspensions, by injection into a vein, muscle or under the skin and topically to the skin. The vehicle will usually form from 0.1% to 99.9%, preferably 90% to 99.9% by weight of the composition and can, in the absence of other adjuncts, form the balance of the composition.

The following formulations are given by way of example only. One skilled in the art will be able to formulate any of the Compounds according to the present invention as they share formulation properties with steroids in common use.

A. Compound G 500 micorgram Tablets

| | |
|---|---|
| Compound G | 0.5% w/w |
| Lactose Ph Eur | 89.5% w/w |
| Povidone (K25) Ph Eur | 5.0% w/w |
| Collloidal Silicon Dioxide Ph Eur | 1.0% w/w |
| Purified Water Ph Eur | 20% w/w * |
| Magnesium Stearate Ph Eur | 1.0% w/w |
| Sodium Starch Glycollate Ph Eur | 3.0% w/w |

* The water is evaporated during the drying process, and does not appear in the finished form.

B. Compound G 2 mg Tablets

| | |
|---|---|
| Compound G | 2.0% w/w |
| Lactose Ph Eur | 88% w/w |
| Povidone (K25) Ph Eur | 5.0% w/w |
| Colloidal Silicon Dioxide Ph Eur | 1.0% w/w |
| Purified Water Ph Eur | 20% w/w * |
| Magnesium Stearate Ph Eur | 1.0% w/w |
| Sodium Starch Glycollate Ph Eur | 3.0% w/w |

* The water is evaporated during the drying process, and does not appear in the finished form.

C. Compound G Sodium Phosphate Injection 4 mg/ml

| | |
|---|---|
| Compound G Sodium Phosphate | 0.4% w/v |
| Sodium Citrate Ph Eur | 1.0% w/v |
| Sodium Bisulphite Ph Eur | 0.2% w/v |
| Sodium Hydroxide | QS * |
| Waters for Injection Ph Eur | To 100% v/v |

* Sodium hydroxide is used to adjust the pH to 7.5-8.5

In order that the present invention may be more readily understood, the following Examples are given, by way of illustration only.

The work described here leading to this invention arose from our studies of the $GR^8$. The results of this work are incorporated into this specification.

EXAMPLE 1

Human Glucocorticoid Receptor Ligand Binding Domain

We used the crystal structure of the human progesterone receptor (PR) as a template for modelling the human glucocorticoid receptor because the two molecules have more than 50% identity in the ligand binding region, and strong sequence similarity. The 12 helices observed in the oestrogen receptor (ER), PR, and retinoic acid receptor (RAER) are all preserved in the human GR. Furthermore the human GR shares the highly conserved aminoacids which make up the nuclear receptor signature[41]. In common with the PR helices 2 and 3 form a contiguous helix as do helices 10 and 11.

The tertiary structure GR ligand binding domain (LBD) containing 251 amino acids (Q527-K777) was predicted using SWISS-MODEL. The result included structural alignment against templates and 3D co-ordinates. It used the 1.8 Å PR LBD dimer (1A28) as a template and the identity between these two LBDs is >50%.

Evaluation of the 3D Structure

The quality verification of this structure was performed using PROCHECK programme, which generates a Ramachandran plot. About 99% of the φ-φ angles in this model were placed within the most favoured and also within allowed regions of the conformational space. The energy analysis of this model was applied the Protein Structure Analysis (Prosa) programmed[42]. This predicts that each residue interaction energy in the structure was negative. The 3D structure predicted for the LBD of the human GR could be superimposed upon that for the PR with a root mean square deviation (rms) of 0.38 Å for 250 $C_\alpha$ atoms.

The ligand binding domain of the human GR (hGR) is outlined by helices 5,7,11 and 12, the β turn and loops L6-7 and L11-12. The ligand binding pocket is predicted to be lined by 18 aminoacids. Of these 15 are predicted to contribute to the hydrophobic environment of the pocket: Met 560, Leu 563, Leu566, Gly567, Trp600, Met601, Met 604, Ala605, Leu608, Phe623, Met 646, Leu732, Tyr735, Thr739, Phe749. There are three polar residues, two at one end of the pocket Gln570 and Arg611 and the other at the opposite end Cys736.

EXAMPLE 2

Fitting of Ligand Within the Predicted Structure

The structure of Dexamethasone was obtained from the Cambridge Structural Database (CSD). We predict that the ligand binding pocket is a longitudinal cleft with two polar residues at one end and a single polar residue at the opposite end. We cannot determine with absolute certainty the orientation of the ligand within the pocket, but several lines of evidence support the orientation of the steroid A ring at the Arg611 end of the pocket. The ligands for both the ER and the PR are orientated in this manner, and both cortisol and aldosterone within the mineralcorticoid receptor are predicted to be in this orientation, based on modelling and mutagenesis studies. The ligand interaction with the receptor was detected using the Ligplot programme, which was also used to plot the interaction. Based on this analysis we predict that the ligand binding domain of the hGR has a three-layered, antiparallel, 12 ∀ helical structure, which is highly homologous to that of the PR. The ligand is bound by three hydrogen bonds; Arg611 and Gln570 interact with the ketone group on C3 of the steroid A ring, and Cys736 to the ketone group on C20 of the D ring. A further 15 aminoacids are found to contribute to hydrophobic interactions with the ligand. Arg611, Gln570 and Cys736 are conserved residues whose importance for ligand binding has been verified by studying either natural or engineered mutants. The aromatic ring of Tyr735 appeared to form a hydrophobic interaction with the ligand. The distance from the aromatic ring to the C22 substituent of the steroid D ring was calculated to be 2.98 A, and to the D ring 3.98 A. However, the hydroxyl group of tyrosine 735 was orientated away from the ligand binding pocket.

EXAMPLE 3

Affinity of Mutant Human GR for Dexamethasone

As Tyr735 was predicted to have hydrophobic interaction with the D ring of Dexamethasone it was important to identify changes in ligand binding affinity caused by the mutations at position 735. Site-directed mutagenesis to phenylalanine (Tyr735phe) resulted in no alteration in ligand binding affinity (4.3 nM compared to 4.6 nM for wild-type), in keeping with the hypothesis that the benzene ring is sufficient to generate a hydrophobic surface for ligand interaction. Change to valine (Tyr735val) resulted in lower affinity binding compared to wild-type, but only to a minor degree (6 nM). The change to serine (Tyr735ser), however, resulted in a two-fold reduction in ligand binding affinity (10.4 nM).

All the mutant receptors were expressed in COS 7 cells, and the mutations did not alter receptor numbers per cell.

EXAMPLE 4

Transactivation by Mutant GR

All three mutant GR molecules were capable of transactivating the MMTV promoter. In response to Dexamethasone Tyr735phe had a similar EC50 to the wild-type (8.6 nM compared to 6 nM) and Tyr735val a lower EC50 14.8 nM. However, the maximal transactivation potential of both of these two mutant GR molecules was less than the wild-type.

The EC50 of Tyr735ser for transactivation was increased to 118 nM, and an accurate estimate of the maximal effect was not possible. It is clear that this effect is disproportionate to the doubling of Kd, suggesting that disruption of ligand binding is insufficient alone to explain the observed change in receptor transactivation.

Further, the physiological ligand hydrocortisone (100 nM) induced 18 fold induction of MMTV via the wild-type GR, 11 fold with the Tyr735Phe, 10.6 fold with the Tyr735Val and failed to induce the reporter via the Tyr735Ser. Thus the mutated receptors have the same rank order of activity with both agonist ligands.

EXAMPLE 5

Transrepression by Mutant GR

Transrepression by activated GR usually has a lower EC50 than transactivation, and places less stringent requirements on the receptor. Hence ligands have been identified which promote transrepression in the absence of transactivation, but not vice versa. We examined the ability of the mutant GR molecules to inhibit NFkB p65 mediated transactivation through a NFkB response element linked to luciferase. The reporter was driven by co-transfection of a p65 expression vector. The wild-type receptor achieved significant suppression at 0.1 nM Dexamethasone and maximal suppression at 1 nM, as did Tyr735Phe and Tyr735Val. Tyr735Ser had a minor, but consistent, increase in IC50 for this effect, with no suppression at 0.1 nM Dexamethasone. These data are compatible with the observed Kd for binding to Dexamethasone, and show the dose-response curve for transrepression to be left-shifted in comparison with transactivation. In contrast to the transactivation data Tyr735Phe and Tyr735Val performed similarly to the wild-type GR, showing that the substitution of Tyr735 results in selective impairment of transactivation in the absence of significant changes in ligand binding affinity and transrepression. Tyr735Ser has a slightly higher IC50 for transrepression compared to the other three GR molecules examined, compatible with the observation that its affinity for Dex is reduced. However, at 100 nM Dex Tyr735Ser has achieved maximal suppression which is close to that observed with the wild-type GR, in striking contrast to the results seen on transactivation.

Figure 1:
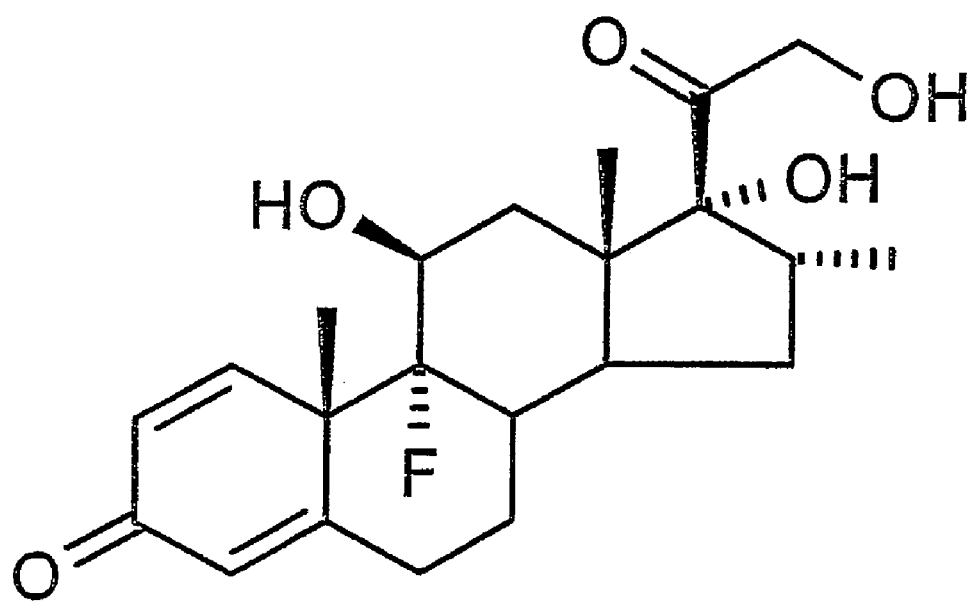
FIG. 1 illustrates the structure of Dexamethasone.

We therefore decided to synthesise a series of compounds with a range of substituents on the D ring as our previous work indicated that the interaction between the D ring of the steroid and tyrosine 735 was essential to transactivation. We also synthesised a number of compounds with modifications at or around the C17 position. The compounds are shown in 2. These compounds and the non-selective glucocorticoid agonist active control molecule, dexamethasone as shown in FIG. 1 were tested for transrepression, transactivation and apoptosis activity as follows:

EXAMPLE 6

In Vitro Assays

Methods

Cell Lines

The COS 7 cell line (ECACC:87021302) is derived from transformed kidney cells of the African green monkey (*Cercopithecus aethiops*). This cell line is deficient in endogenous GR and is therefore used widely as a tool to study GR function by controlled artificial expression via transfection.

The A549 cell line (ECACC:86012804) is derived from the human lung epithelial cells from a carcinoma. This cell line contains functional endogenous GR and is stimulated by Tumour Necrosis Factor (TNF) to produce IL-8.

The HEP G2 cell line (ECACC: 85011430) is derived from human liver epithelial cells from a well differentiated hepatocellular carcinoma. This cell line has functional endogenous GR and is stimulated by GR activation to produce tyrosine amino transferase.

The CEM-C7A cell line is a steroid sensitive clone of the CCRF-CEM cell line (ECACC 85112105). This is a T lymphoblastoid cell line with functional endogenous GR.

COS 7 cells and A549 cells were cultured in DMEM with Glutamax (Gibco BRL, Paisley, UK), and 10% fetal calf serum (FCS). HEP G2 were cultured in DMEM with Glutamax (Gibco BRL), 1% non-essential amino acids (Gibco BRL) and 10% FCS. CEM-C7A cells were cultured in Optimem (Gibco BRL) with 5% FCS.

Plasmids
pcDNA3-GR
AH3-Luc
NRE-Luc
P65

Lipofectamine Transfection

All transfections were performed using lipofectamine plus (Gibco BRL), according to the manufacturers' instructions, as previously described[1]. Briefly, all cells were seeded at $5\times10^5$ per 10 cm tissue culture plate 18 hours before transfection, the next day the relevant plasmids were mixed with serum free medium and "Plus" reagent (Gibco BRL) and incubated for 15 mins, lipofectamine reagent was added and the mix was incubated for a further 15 mins, this mix was added to the cells on serum free medium in the 10 cm tissue culture plates and left for 3 hours, the cells were then trypsinised and divided into 24 well plates, the cells were left to recover overnight and were treated with steroid for 16 hours before harvest. All experiments were performed from one transfection in triplicate and on separate occasions with similar results.

Luciferase Assay

The firefly luciferase gene catalyses the production of light from the substrate luciferin. When plasmid constructs containing this gene are transfected into cell lines the activity of the gene can be assessed by the intensity of the luminesence. The luciferase assay yields luminescence through an ATP-dependent oxidation of luciferin the amount of light produced can be measured by a luminometer and is a measure of gene activity (Davis, 1996). Light intensity was measured in a Luminometer (LB 9501, Berthold). The light intensity should be proportional to luciferase concentration in the range of $10^{-16}$M (10 µg/L) to $10^{-8}$M (1 mg/L). To measure the luminescence of the treated cells 150 µl of 1× reporter lysis buffer (RLB: 25 mM Tris phosphate pH7.8, 10 mM MgCl$_2$, 15% Glycerol, 1% Triton, 1 mM EDTA) was added to the 24 well plates to lyse the cells and incubated at room temperature for 30 mins whilst being shaken. Then 100 µl of the room temperature cell extract were mixed with 100 µl of room temperature Luciferase Assay Reagent (LAR: 1 mM ATP, 0.3 mM D-Luciferin, 66% RLB). This reaction was mixed in a luminometer (LB 9501, Berthold) and the light produced was measured for a period of 5 seconds.

(a) Transactivation Assay Using Artificially Expressed Glucocorticoid Receptor in the COS 7 Monkey Kidney Cell Line In this assay the GR was artificially expressed in a cell line lacking endogenous GR and a glucocorticoid response element (GRE) "driving" a luciferase reporter gene was used to measure ligand dependent activation.

COS7 cells were transfected with 1 µg pcDNA3-GR and 3 µg AH3-Luc per 10 cm tissue culture dish. The cells were plated out in to 24 well plates after transfection and the steroids were added immediately. After 18 hour incubation the cells were lysed and a luciferase assay was performed.

(b) SRC-1 Association Assay by Mammalian Two-Hybrid Analysis

SRC-1 is an important co-activator of GR action that associates with the GR in a ligand dependant manner. The ability of SRC-1 to associate with the GR in this manner can be used as a measure of potency of ligand mediated transactivation. To perform this assay plasmids that generated VP16-GR ligand binding domain (LBD) and GAL4-SRC-1 fusion proteins and a GAL4 binding luciferase reporter gene construct were transfected into in a cell line lacking GR and deficient in endogenous SRC-1. The GAL4-SRC-1 fusion protein could bind to specific sites upstream of the luciferase reporter gene construct. If the SRC-1 fusion protein associated with the ligand bound VP16-GRLBD fusion protein then the VP-16 activation domain augmented the luciferase gene expression. Ligand dose responses were analysed for SRC-1 binding for the compounds shown in FIGS. 1 and 2A.

(c) Quantitation of Endogenous Tyrosine Amino Transferase (TAT) Protein in the HEPG2 Liver Cell Line In this method a colourimetric approach is used to quantitate TAT activity. The TAT enzyme catalyses the following reaction:

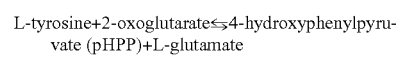
L-tyrosine+2-oxoglutarate⇌4-hydroxyphenylpyruvate (pHPP)+L-glutamate

This reaction also requires pyridoxal phosphate (PLP) as a co-factor.

Strong alkali conditions can then be used to convert pHPP to p-hydroxybenzaldehyde (pHBA) and oxalate. The amount of pHBA can then be assessed by measuring its absorbance at 331 nm (extinction coefficient 19,900 $M^{-1}cm^{-1}$) this figure is then assumed to be directly proportional to TAT activity. HEPG2 cells were cultivated till confluent on a 10 cm plate (~$10^7$ cells). These cells were then scraped off and suspended in 500 µl of ice cold 0.14M KCl. The cells were lysed by 3 cycles of 10 second burst sonication at full power (50 W, 20 kHz Sonicator; Jencons, Leighton Buzzard, UK). The cells were kept on ice between each burst. The debris in the lysed cell suspension was then spun down (13000 rpm, 20 mins; microfuge) and the protein concentration of the supernatant was assayed using the Bradford method. 100 µg of protein was then used to assay the TAT activity.

To perform the TAT assay the following reaction mix was made up in a 1.5 ml eppendorf:

| | |
|---|---|
| 900 µl | 7 mM L-Tyrosine in 0.2M $KPO_4$ |
| 30 µl | 0.3M Ketoglutarate |
| 30 µl | 1.2 mM PLP |
| ? | 100 µg of cellular protein |
| ? | 0.2M $KPO_4$ |
| 1000 µl | |

For each reaction a control reaction was set up without the ketoglutarate. The samples were incubated at 37° C. for 20 minutes and then 60 µl of 10M NaOH was added. The samples were incubated at room temperature for a further 30 mins and then the absorbance of each sample was assessed at 331 nm on a spectrophotometer (Ultrospec III, Pharmacia).

(d) Transrepression Assay Using Artificially Expressed Glucocorticoid Receptor and P65 in the COS 7 Monkey Kidney Cell Line To perform this assay the GR and p65 were artificially expressed in a cell line lacking GR and deficient in endogenous P65. The ability of P65 to activate an NFkB response element (NRE) "driving" a luciferase reporter gene could then be repressed by GR in a ligand dependent manner and, therefore, used to measure transrepression.

COS7 cells were transfected with 1 µg pcDNA3-GR and 3 µg NRE-Luc and 200 ng p65 per 10 cm tissue culture dish. The cells were plated out in to 24 well plates after transfection and left for 18 hours to recover before the steroids of FIGS. 1 and 2A were added. After another 18 hour incubation the cells were lysed and a luciferase assay was performed.

(e) Transrepression Assay Using Endogenous GR in the A549 Lung Epithelial Cell Line In this assay TNF was used to stimulate NFkB activity in a cell line that expressed endogenous GR. The ability of NFkB to activate an NRE "driving" a luciferase reporter gene could then be repressed by GR in a ligand dependent manner and, therefore, used to measure transrepression.

COS7 cells were transfected with 3 µg NRE-Luc per 10 cm tissue culture dish. The cells were plated out in to 24 well plates after transfection and left for 18 hours to recover before the steroids of FIGS. 1 and 2 were added. Next TNF was added to the samples after 3 hours incubation with the steroids and after another 15 hours the cells were lysed and a luciferase assay was performed.

(f) Repression of Endogenous IL-8 in A549s

In this assay TNF was used to stimulate NFkB activity in a cell line that expressed endogenous GR. The ability of NFkB to induce IL-8 gene transcription could then be repressed by GR in a ligand dependent manner and, therefore, used to measure transrepression.

COS7 cells were transfected with 3 µg NRE-Luc per 10 cm tissue culture dish. The cells were plated out in to 24 well plates after transfection and left for 18 hours to recover before the steroids of FIGS. 1 and 2A were added. After incubation for 3 hours with the steroids, TNF was added to the samples and after another 15 hours an IL-8 assay (R&D systems) was performed on the cell supernatants according to the manufacturers instructions. Briefly, triplicates of 100 µl of a 1:2 dilution of cell supernatant and 100 µl of a known dilution series of IL-8 were added to the wells of a microtitre plate coated with a monoclonal IL-8 antibody, the samples were incubated with a polyclonal biotinylated IL-8 antibody for 1 hour at room temperature and washed. Streptavidin horse radish peroxidase solution was then added to all wells and incubated for 30 mins before being washed. Tetramethyl benzidine (TMB; a chromagen) was added to all the wells and incubated in the dark for 10 mins, the reaction was stopped by the addition of $H_2SO_4$ and the absorbance of each well was read on a spectrophotometer using 450 nm as the primary wavelength. Regression analysis was performed on the standard data and the unknowns were expressed as pg/ml of IL-8 in comparison to the standards.

(g) Assessment of Nuclear Translocation Using GFP Tagged GR and Fluorescent Microscopy.

The un-liganded GR is present in the cytoplasm of cells in association with heat shock proteins (HSPs). The binding of an agonist ligand to the GR causes dissociation from the HSPs and translocation to the nucleus. A type I antagonist ligand can bind to the GR but cannot translocate to the nucleus. A type II antagonist ligand can bind to the GR, translocate to the nucleus and bind to DNA but cannot activate gene transcription. Therefore, the ability of a putative ligand to translocate the GR helps to determine its status as an agonist or antagonist. COS 7 cells were transfected with 5 µg of a green fluorescent protein (GFP) tagged GR expression vector. After transfection, these cells were split into 6 well plates with sterile microscope cover slips placed at the bottom of each well. The cells were allowed to recover for 18 hours and then the medium was removed, the cells were washed three times with sterile phosphate buffered saline (PBS) and new medium was added containing charcoal stripped FCS in place of normal FCS. The cells were incubated for 18 hours and then the steroids of FIGS. 1 and 2A were added to make a final concentration of 100 nM. The cells were incubated for a further 3 hours and then the medium was aspirated and the cells were fixed to the glass coverslips by adding ice cold methanol and incubating at −20° C. for 30 mins. The coverslips with the transfected cells fixed to them were mounted on slides and the cellular localisation of the GFP tagged GR was analysed by fluorescent microscopy using an Axioplan 2 microscope (Zeiss, Oberkochen, Germany) and KS300 v3.0 analysis software (Zeiss).

(h) Type II Antagonist Activity Assay: Competition of Dexamethasone Transactivation.

A type II antagonist should be able to compete agonist activity. As an antagonist has no ability to transactivate, competition can be measured by inhibition of an agonist in a transactivation assay. RU486 is a type II antagonist of GR function and can compete against the agonist dexamethasone for ligand binding, this interaction can be used as a positive control for this analysis.

As with the standard transactivation assay previously described, the GR was artificially expressed in a cell line lacking endogenous GR and a GRE "driving" a luciferase reporter gene was used to measure ligand dependent activation. COS7 cells were transfected with 1 μg pcDNA3-GR and 3 μg AH3-Luc per 10 cm tissue culture dish. The cells were plated out in to 24 well plates after transfection and the steroids were added immediately. All wells except the negative control were treated with 50 μM dexamethasone to generate a final concentration of 100 nM. Certain steroids from FIG. 2A were added at the same concentration to all sample wells. After 18 hour incubation the cells were lysed and a luciferase assay was performed.

(i) Progestogen Activity Assay Using Progesterone Receptor Transactivation.

As the GR LBD has strong homology with the PR LBD there is a chance that any of the tested steroids of FIGS. 1 and 2A that activate one of these receptors may also activate the other. The presence of illegitimate progestogen activity associated with the steroids of FIGS. 1 and 2A was examined using a transactivation assay with the PR instead of the GR.

The PR was artificially expressed in a cell line lacking endogenous PR and a GRE "driving" a luciferase reporter gene was used to measure ligand dependent activation.

COS7 cells were transfected with 1 μg pSEO-PRB and 3 μg AH3-Luc per 10 cm tissue culture dish. The cells were plated out in to 24 well plates after transfection and the steroids of FIGS. 1 and 2A were added immediately to generate a final concentration of 100 nM. After 18 hour incubation the cells were lysed and a luciferase assay was performed.

(j) Apoptosis Assay

Apoptosis (programmed cell death) is mediated by a protein called Bax the transcription of which is primarily controlled by the GR in a ligand dependant manner. To measure the ability of a GR ligand to effect apoptosis a suitable cell line was incubated with ligand and a viable cell count was performed after three days.

CEM-C7A cells were plated out on to a 96well plate at $5 \times 10^5$/well. The steroids of FIGS. 1 and 2A were added immediately to generate a final concentration of 100 nM. After a three day incubation the live cell number in each well was assessed using Celltiter 96 Aqueous Non-Radioactive Cell Proliferation Assay (Promega). This assay is a calorimetric method for determining the number of viable cells in proliferation or chemosensitivity assays.

Briefly, the assay is composed of solutions of a novel tetrazolium compound (3-(4,5-dimethylthiazol-2-yl)-5-(3-carboxymethoxyphenyl)-2-(4-sulfophenyl)-2H-tetrazolium, MTS) and an electron coupling reagent (phenazine methosulfate; PMS). MTS is bioreduced by cells into a formazan product that is soluble in tissue culture medium. The absorbance of the formazan at 490 nm can be measured directly from 96 well assay plates without additional processing. The conversion of MTS into aqueous, soluble formazan is accomplished by dehydrogenase enzymes found in metabolically active cells. The quantity of formazan product as measured by the amount of 490 nm absorbance is directly proportional to the number of living cells in culture.

Results

Compounds were tested in two batches as follows:
Batch 1: Compounds A, H and D. Compounds C and E proved too insoluble to give reproducible results and no data are presented on these compounds.

Batch 2: Compounds G to T inclusive.
In all instances, dexamethasone, the structure of which is shown in FIG. 1, was included as an active control.

Figure 3:
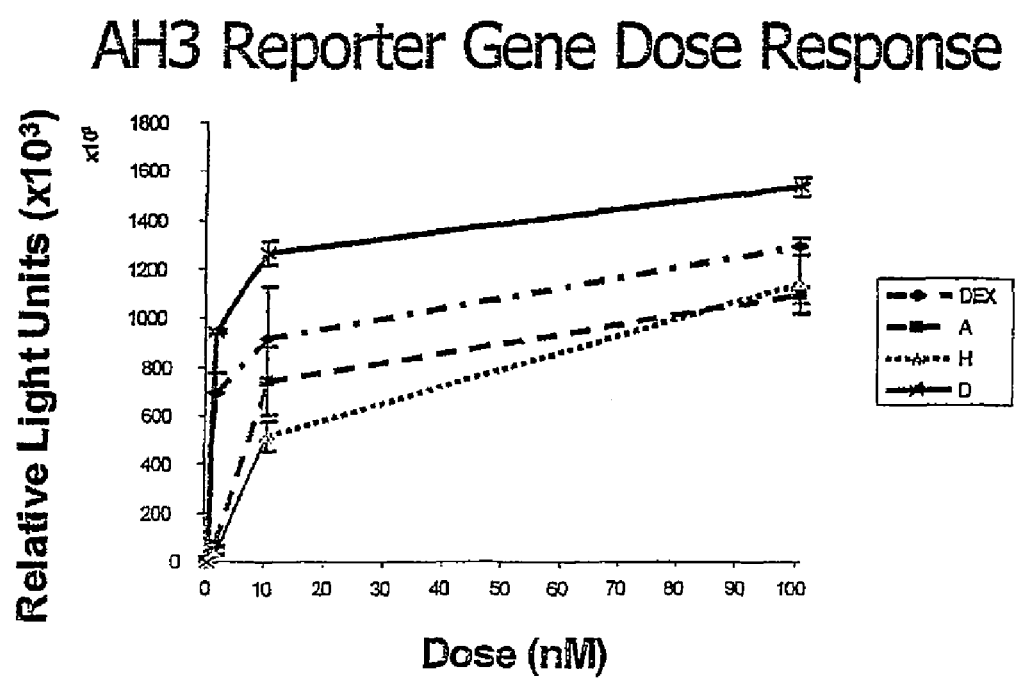
FIG. 3 illustrates the dose response of dexamethasone and Compounds A, H and D in a transactivation assay (luminescence) using artificially expressed glucocorticoid receptor in the COS 7 monkey kidney cell line.

Ligand Induced Transactivation by the Glucocorticoid Receptor (a) Transactivation Assay Using Artificially Expressed Glucocorticoid Receptor in the COS 7 Monkey Kidney Cell Line The ability of all the compounds set out in FIG. 2A to transactivate was first examined at 1, 10 and 100 nM (FIGS. 3 and 4.). Compound D appeared to be more active in causing transactivation than dexamethasone (FIG. 3). It was found that compounds L, O, Q and R failed to generate a response at any concentration. Compound G was much less potent and had a lower maximal effect when compared to dexamethasone. All the other compounds showed some ability to transactivate with differing maximal induction although this response was "right shifted" compared to dexamethasone (FIGS. 3 and 4.).

To further examine the transactivation potential of the tested compounds this experiment was repeated at 1, 10, 10 and 500 nM with the compounds that had generated some response in the first experiment (i.e. all except L, O, Q and R). This experiment confirmed that compounds H, I, J, K, M, N and S had a similar maximal response compared to dexamethasone although they all responded with a "right shift" (FIG. 5.). Compounds G, P and T had a "right shifted response" and a reduced maximum compared to dexamethasone, although this was only slight in the case of T (FIG. 5.). Compound G had the lowest overall maximal response and also the lowest response at any dose compared to the other compounds (FIG. 5.).

(b) SRC-1 Association Assay by Mammalian Two-Hybrid Analysis

Figure 6:
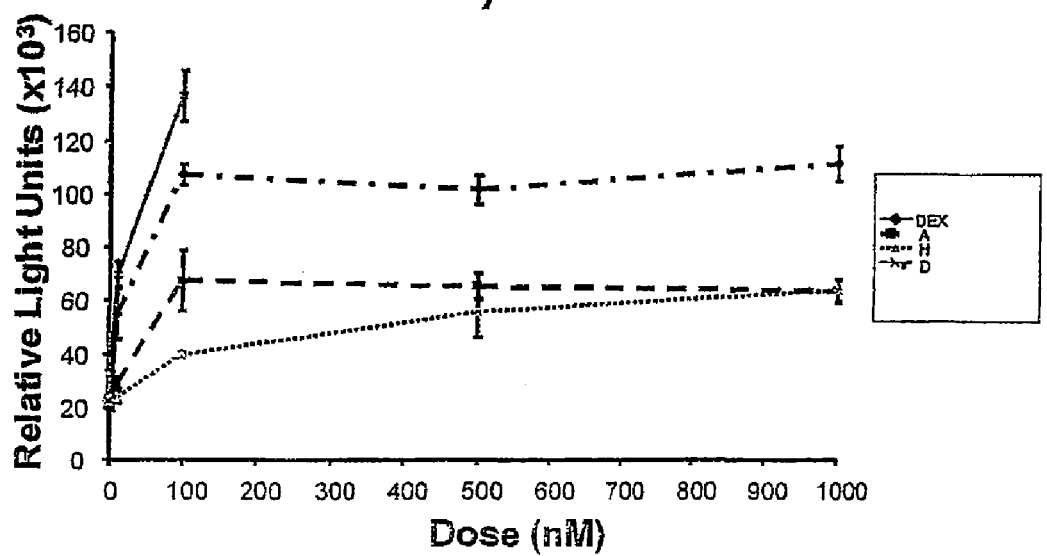
FIG. 6 illustrates the dose response of dexamethasone and Compounds A, H and D in a SRC-1 association (luminescence) assay by mammalian two-hybrid analysis.

The ability of all the compounds shown in FIG. 2A to recruit SRC-1 was tested against dexamethasone. They were tested at 1, 10 and 100 nM concentrations (FIGS. 6 and 7). It was found that only compound D recruited SRC-1 to the same extent as dexamethasone. Compound A produced a submaximal response (~50%). At the clinically relevant concentrations of 1 and 10 nmolar, compound G caused no transactivation as measured by SRC-1 recruitment. Even at the highest concentration tested, compound G caused no SRC-1 recruitment. None of the rest of the compounds recruited SRC-1 as well as dexamethasone and only compounds J, K, R, S and T generated a significant response at 100 nM.

Figure 8:
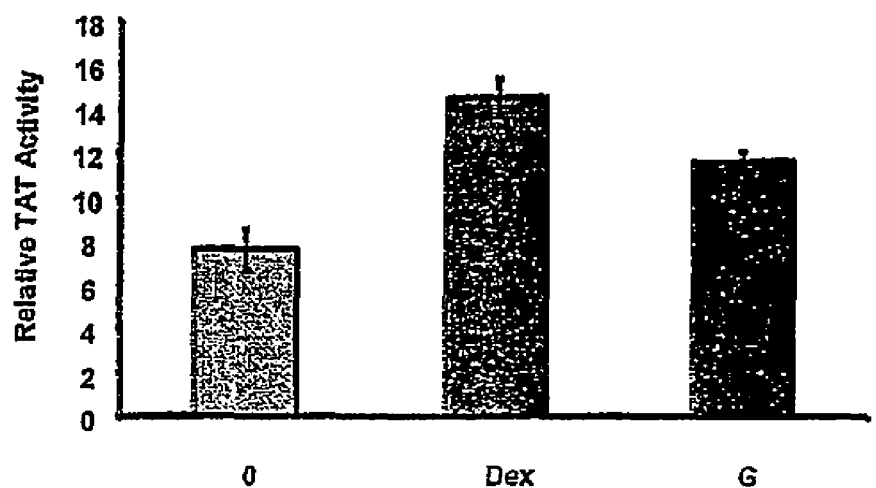
FIG. 8 illustrates the ability of compound G to activate the endogenous tyrosine amino transferase (TAT) gene as compared with dexamethasone at concentrations of 100 μM.

(c) Quantitation of Endogenous Tyrosine Amino Transferase (TAT) Protein in the HEPG2 Liver Cell Line The ability of compound G to activate the endogenous tyrosine amino transferase (TAT) gene was compared with dexamethasone at a concentration of 1 μM. It was found that there was a significant reduction in TAT activity using compound G as the GR ligand compared to dexamethasone (p=0.014, two tailed t-test) (FIG. 8).

Figure 9:
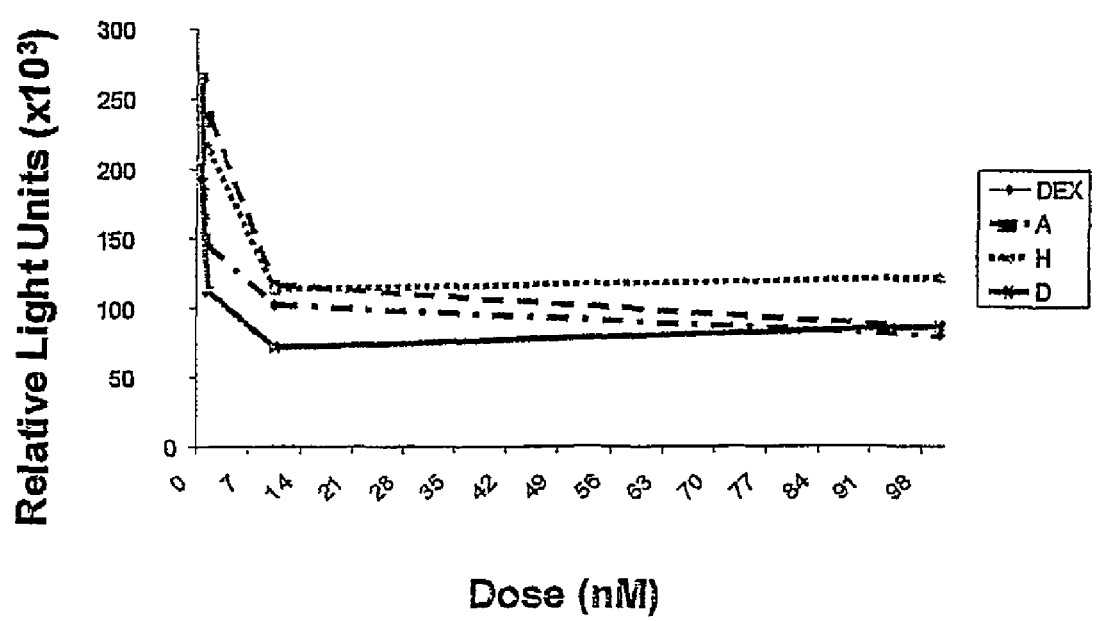
FIG. 9 illustrates the dose response of dexamethasone and Compounds A, H and D in a transrepression assay (luminescence) using artificially expressed glucocorticoid receptor and P65 in the COS 7 monkey kidney cell line and demonstrates the ability of the tested compounds to repress P65 stimulation of an NFkB response element.

Ligand Induced Transrepression by the Glucocorticoid Receptor (d) Transrepression Assay Using Artificially Expressed Glucocorticoid Receptor and P65 in the COS 7 Monkey Kidney Cell Line The ability of the compounds of FIG. 2A to repress P65 stimulation of an NFkB response element was examined at 1, 10 and 100 nM (FIGS. 9 and 10.). Compounds A and H were less potent than dexamethasone but produced the same maximal response at 100 nM. Compound D was as potent as dexamethasone (FIG. 9). In the second series of compounds, it was found that only three of the compounds (L, O and R) failed completely to repress P65 function but several compounds demonstrated no effect at 1 and 10 nM with only a negligible repression at 100 nM (J, P and Q). The remaining compounds all repressed P65 at least as well as dexamethasone with a "left shifted" response and greater maximal repression in the case of compounds G and T.

Figure 11:
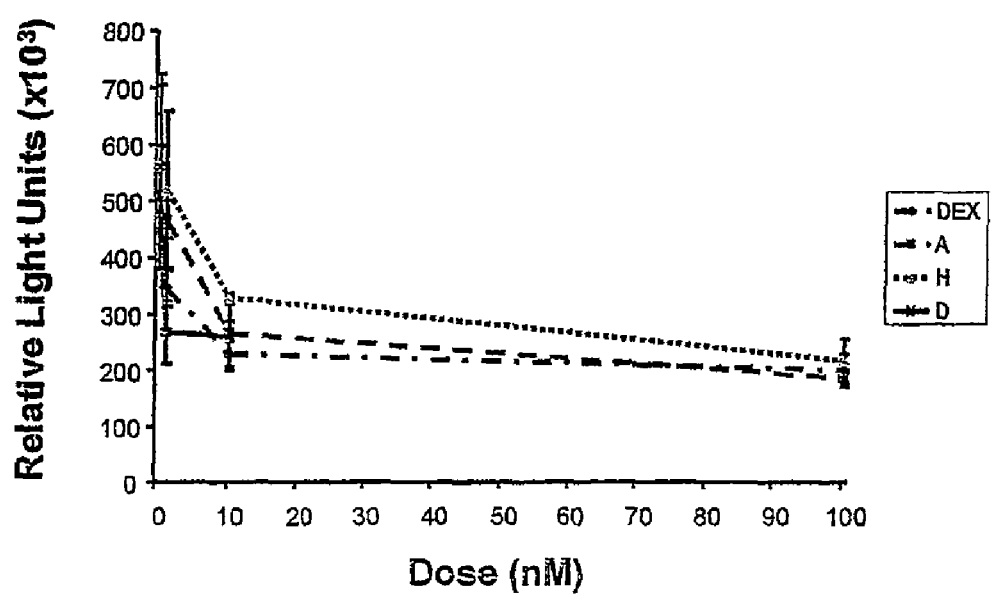
FIG. 11 illustrates the dose response of dexamethasone and Compounds A, H and D in a transrepression assay (luminescence) using endogenous glucocorticoid receptor in the A549 Lung Epithelial Cell Line and demonstrates the ability of the tested compounds to transrepress TNF activation in A549 cells.

(e) Transrepression Assay Using Endogenous GR in the A649 Lung Epithelial Cell Line The ability of the compounds of FIG. 2A to transrepress TNF activation in A549 cells is shown in FIGS. 11 and 12. The ability of compound G to repress TNF activation of A549 cells was examined using an NRE reporter gene and 1, 10, 100 and 500 nM of compound. It was found that compound G repressed at least as well as dexamethasone and also had a "left shifted" response with greater maximal repression. Compounds A D and H were also assessed in this assay. All compounds exhibited transrepression.

(f) Repression of Endogenous IL-8 in A549s

Figure 13:
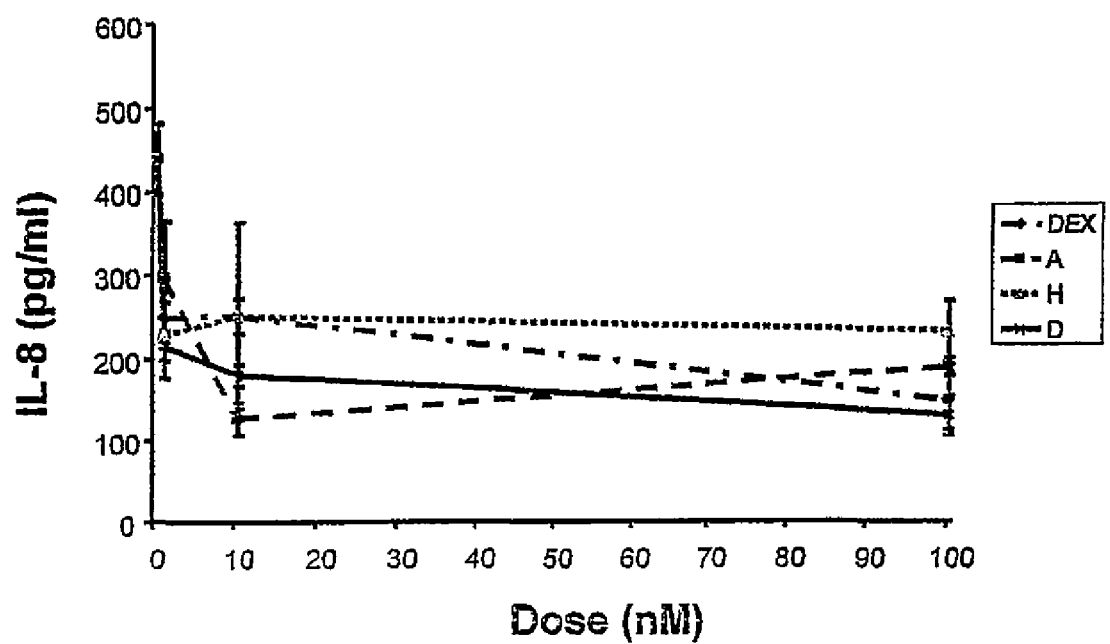
FIG. 13 illustrates the dose response of dexamethasone and Compounds A, H and D in a transrepression assay (luminescence) of endogenous IL-8 in A549 Lung Epithelial Cells and demonstrates the ability of the tested compounds to transrepress IL-8 activation in A549 cells.
Figure 14:
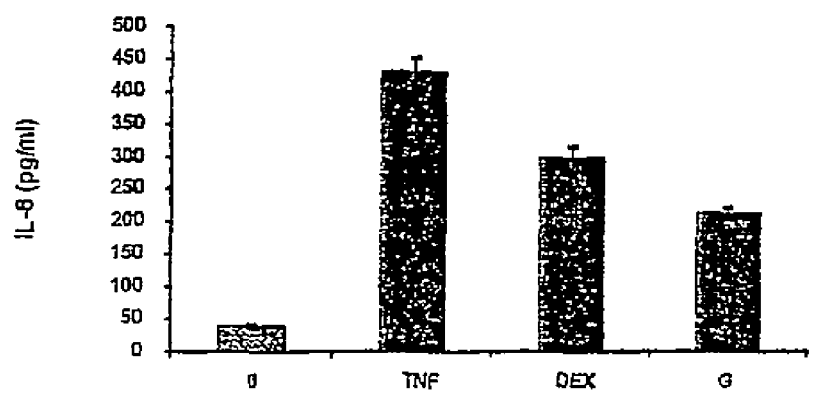
FIG. 14 illustrates the repression data for TNF, dexamethasone and Compound G in the transrepression assay (luminescence) of endogenous IL-8 in A549 Lung Epithelial Cells.

The ability of the compounds of FIG. 2A to transrepress IL-8 activation in A549 cells is shown in FIGS. 13 and 14. The ability of 100 nM compound G to repress TNF activation of A549 cells was also examined using IL-8 production as an endogenous end point. It was found that compound G repressed IL-8 production better than dexamethasone (p=0.0076, two tailed t-test). Compounds A, D and H exhibited transrepression in this assay.

(g) Assessment of Nuclear Translocation Using GFP Tagged GR and Fluorescent Microscopy.

Figure 15:
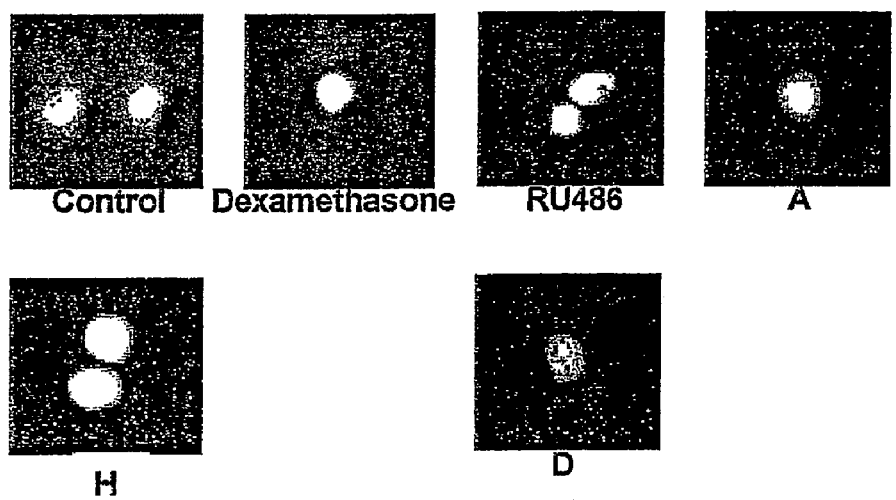
FIG. 15 illustrates the nuclear translocation associated with dexamethasone, RU486 and Compounds A, H and D using GFP tagged glucocorticoid receptor and fluorescent microscopy.

Compounds A, H and D caused nuclear localisation of the GFP tagged glucocorticoid receptor, therefore they are all capable of GR binding (FIG. 15). The ability of certain compounds from the second set of compounds to cause translocation is shown in FIG. 16. Compound O failed to cause translocation, consistent with inactivity in all of the other assays and the conclusion that this compound did not bind to the glucocorticoid receptor. The other compounds tested caused translocation of the receptor to the nucleus.

(h) Type II Antagonist Activity Assay: Competition of Dexamethasone Transactivation.

Four putative antagonists were identified by their lack of function in either transactivation or transrepression assays (L, O, Q and R). To check for type II antagonist function the ability of these compounds to compete with dexamethasone for GR binding was assessed using RU486, a well-defined GR type II antagonist, as a positive control. COS7 cells were transfected with a transactivation sensitive reporter gene and were then stimulated with 1 nM dexamethasone. RU486 (1, 10, 100 nM) competed dexamethasone function in a dose dependent manner with a maximal repression of transactivation of ~50%. Compounds L, O, Q and R failed to repress dexamethasone transactivation and, therefore, failed to act as competitive antagonists (FIG. 17).

(i) Progestogen Activity Assay Using Progesterone Receptor Transactivation.

Illegitimate progestogen activity exhibited by the compounds as shown in FIG. 18 was examined by a transactivation assay using the AH3-luc reporter and a PRB expression vector. In this system 100 nM progesterone caused a strong induction of the reporter gene whereas 100 nM dexamethasone caused very little increase in reporter gene activation over the negative control. Compounds G, H, I and P exhibited a similar or decreased reporter gene activation compared to that of dexamethasone. Compounds J, K, L, M, N, O, Q, R, S and T exhibited a slightly increased reporter gene activation compared to that of dexamethasone. None of the compounds demonstrated the potency of progesterone at PRB activation, the strongest, L, only demonstrated ~40% the activation generated by progesterone.

(j) Apoptosis Assay

Figure 20:
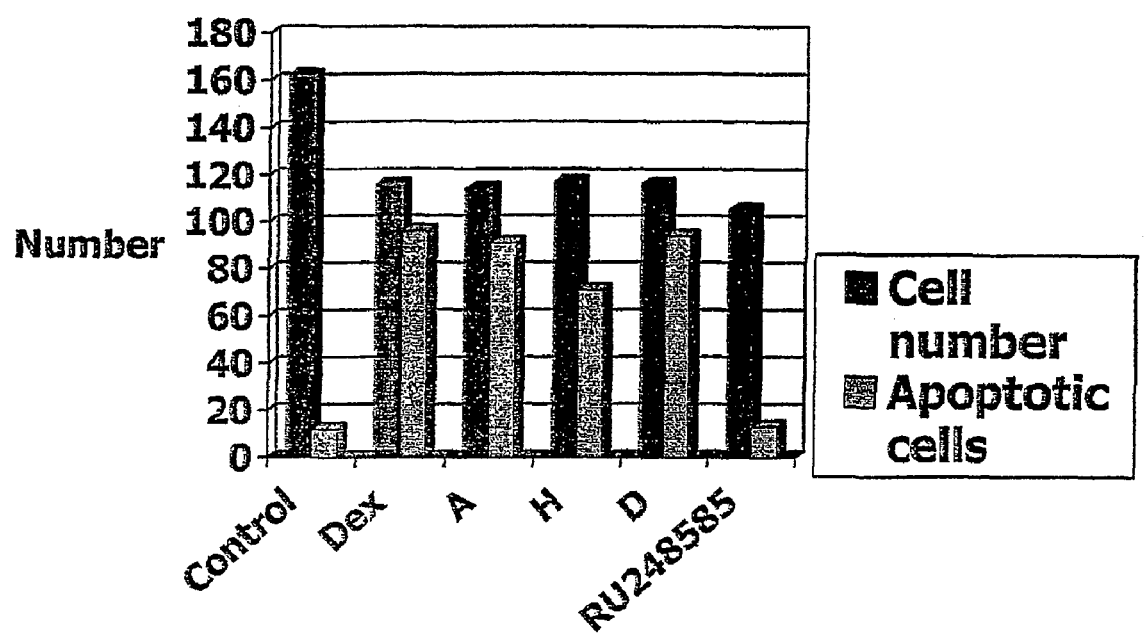
FIG. 20 illustrate the results of an apoptosis assay comparing Compounds A, H and D with dexamethasone and RU248585.
Figure 21:
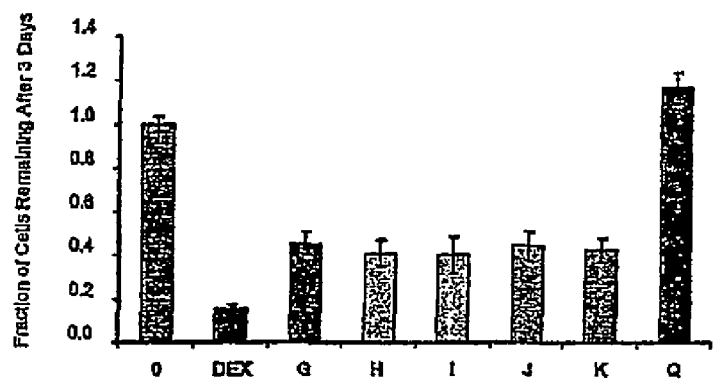
FIG. 21 illustrates apoptosis results in CEM C7A cells using dexamethasone and Compounds G through K and Q.

CEM C7A cells are a human T lymphoblast cell line which undergoes apoptosis in response to glucocorticoid. The exact mechanism is uncertain, but likely relates to the lymphocytolytic action of glucocorticoid in vivo, and may model aspects of glucocorticoid mediated anti-inflammation. In the first series of compounds, Dexamethasone and compound A were the most potent inducers of apoptosis. RU24858 impaired proliferation but did not induce significant apoptosis (FIG. 20). We have extensive previous data using RU24858, and it consistently fails to induce apoptosis. In the second series of compounds, apoptosis was induced by G to K but not by compound Q. This last compound had no activity in any of the assays and is thought not to bind. The fact that apoptosis was induced by the highly selective compound, compound G, which is essentially lacking in transactivation activity but has high transrepression activity was an unexpected finding and in contrast with the activity of other selective agonists such as RU24858.

EXAMPLE 7

Ligand Binding Assays

Binding of compound G to the glucocorticoid receptor was investigated using a standard competition assay. The conditions were as follows:

| | |
|---|---|
| Source | Human HeLa 53 cells |
| Ligand | 6 nM $^3$H Dexamethasone |
| Vehicle | 0.4% DMSO |
| Incubation time/temp | 2 hours @25° C. |
| Incubation buffer | RPMI 1640, 10 nM Hepes, pH 7.2 |
| Non-specific ligand | 20 μM Dexamethasone |
| Kd | 5 nM |
| $B_{max}$ | 61000R/cell |
| Specific binding | 75% |
| Quantitation method | Radiological binding |
| Significance criteria | >50% of max stimulation or inhibition. |

$IC_{50}$ values were determined by a non-linear, least squares regression The $K_I$ values were calculated using the equation of Cheng and Prusoff using the observed $IC_{50}$ of the test compound, the concentration of radioligand employed in the assay, and the historic values for the $K_d$ for the ligand. The Hill coefficient ($n_H$), defined as the slope of the competitive binding curve, was calculated.

Compound G bound to the glucocoticoid receptor. The binding curve was right shifted when compared to dexamethasone. This was a surprising finding as, in the transrepression assays, Compound G was at least as effective as dexamethasone. It is possible to speculate that the binding in this assay is more reflective of the transactivational activity of the compounds than the transrepressive activity of the compounds.

Compound G was also shown not to bind to the progesterone receptor in a classic receptor binding assay (data not shown). Compound G was also shown not to bind to other members of the steroid receptor super family. Interestingly, in a classic receptor binding assay (FIG. 19), Compound G appeared to be a less potent ligand than dexamethasone for the GR so the findings in both the in-vitro and in-vivo assays were surprising, with Compound G showing the same or greater activity in transrepression.

EXAMPLE 8

In-Vivo Assays

To test further the validity of the in-vitro models as predictors of in-vivo anti-inflammatory effects and in-vivo induction of protein synthesis (transactivation), Compound G was studied in a classical animal model of inflammation.

Male outbred Swiss albino mice (18-20 g body weight) were purchased from Bantin and Kingman (T.O. strain; Hull, Humberside) and maintained on a standard chow pellet diet with tap water ad libitum and a 12:00 h light/dark cycle. All animals were housed for 3 days prior to experimentation to allow body weight to reach 20-22 g. On the day of experiment mice ranged from 24-26 g.

Air-pouches were formed on the back of mice by air injection (2.5 ml s.c.) on day 0 and day 3 (Perretti and Flower, 1993).

On day 6 mice were subjected to vehicle (300 µl, groups A and D), or treated with dexamethasone (3 µg, group B) or compound G (3 µg, group C) at −1 h injected intra-peritoneal (i.p.), group E was left untreated. Compound G and Dexamethasone were prepared by diluting stock solutions in DMSO in paraffin oil (final DMSO concentration, less than 0.01%).

Zymosan A was allowed to defrost at room temperature for 30 min prior to being added to sterile PBS at a concentration of 2 mg/ml forming a homogenous suspension.

At time 0, mice received either 0.5 ml of zymosan (1 mg) (group A, B, C) injected locally into the air-pouch. Group D and E were left untreated at this time-point. At 4 h post-zymosan the animals were placed in $CO_2$. Air-pouches were then washed with 2 ml of PBS containing 3 mM EDTA, and livers were recovered and snap frozen for later analysis.

The number of migrated leukocytes ($\geq$90% polymorphonuclear leukocytes, PMN) was determined in the lavage fluid from each air-pouch, by taking an aliquot (100 µl) of the lavage fluid and diluting 1:10 in Turk's solution (0.01% crystal violet in 3% acetic acid). The samples were then vortexed and 10 µl of the stained cell solution were placed in a Neubauer haematocymometer and neutrophils numbers counted using a light microscope (Olympus B061).

Quantitation of Tyrosine Amino Transferase (TAT) Protein in the Livers: In this method a colourimetric approach is used to quantitate TAT activity. The TAT enzyme catalyses the following reaction:

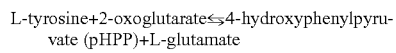

This reaction also requires pyridoxal phosphate (PLP) as a co-factor. Strong alkali conditions can then be used to convert pHPP to p-hydroxybenzaldehyde (pHBA) and oxalate. The amount of pHBA can then be assessed by measuring its absorbance at 331 nm (extinction coefficient 19,900 $M^{-1}cm^{-1}$) this figure is then assumed to be directly proportional to TAT activity. Livers were homogenized and the cells were stored on ice. The debris in the lysed cell suspension was then spun down (13000 rpm, 20 mins; microfuge) and the protein concentration of the supernatant was assayed using the Bradford method. 100 µg of protein was then used to assay the TAT activity. To perform the TAT assay the following reaction mix was made up in a 1.5 ml eppendorf:

| | |
|---|---|
| 900 µl | 7 mM L-Tyrosine in 0.2M $KPO_4$ |
| 30 µl | 0.3M Ketoglutarate |
| 30 µl | 1.2 mM PLP |
| ? | 100 µg of cellular protein |
| ? | 0.2M $KPO_4$ |
| 1000 µl | |

For each reaction a control reaction was set up without the ketoglutarate. The samples were incubated at 37° C. for 20 minutes and then 60 µl of 10M NaOH was added. The samples were incubated at room temperature for a further 30 mins and then the absorbance of each sample was assessed at 331 nm on a spectrophotometer (Ultrospec III, Pharmacia).

Experimental groups are described below:
  group A, vehicle i.p.+zymosan intra-pouch, n=8
  group B, dexamethasone+zymosan intra-pouch, n=8
  group C, compound G+zymosan intra-pouch, n=8
  group D, vehicle i.p., n=8
  group E, no treatment, n=8

Statistics

Neutrophil numbers were compared between groups using ANOVA plus the Bonferroni test. TAT levels were compared using a t-test.

Figure 22:
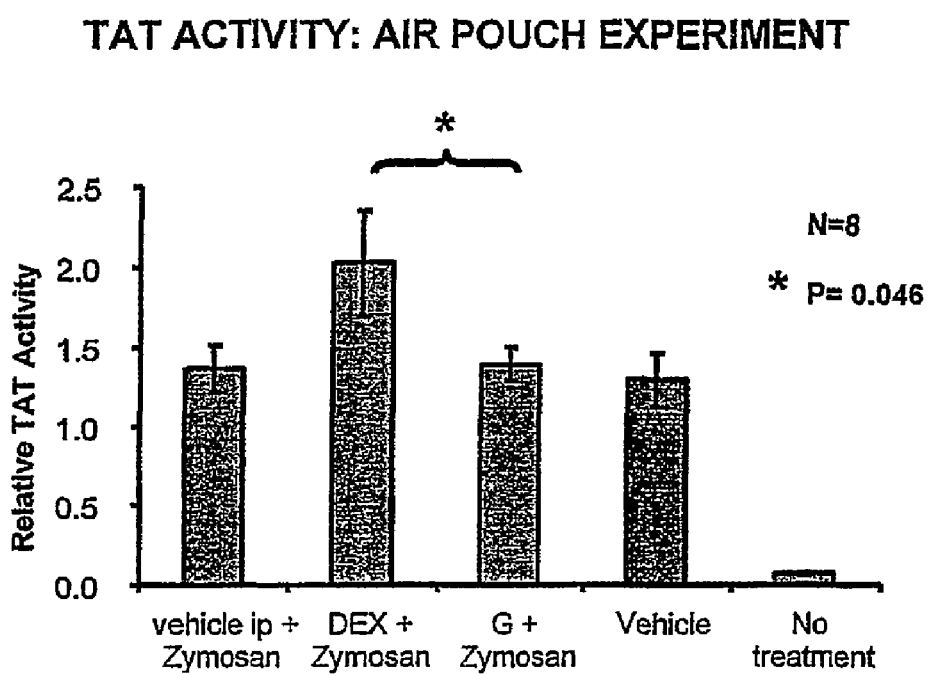
FIG. 22 presents the results of in vivo testing with mice using a classical air pouch animal model of inflammation and measuring TAT activity using dexamethasone and Compound G.

The results of the neutrophil accumulation are shown in table I below and the TAT assay in FIG. 22.

TABLE 1

Effect of compound G on zymosan induced neutrophil migration ($10^6$ per mouse) as evaluated at the 4 h time-point (cumulative data).

| Experimental Group | Stimulus | Neutrophils ($10^6$ per mouse) |
|---|---|---|
| A (vehicle) | Zymosan 1 mg | 9.15 ± 0.92 |
| B (Dexamethasone) | Zymosan 1 mg | 6.23 ± 0.44 * |
| C (Compound G) | Zymosan 1 mg | 6.33 ± 0.79 * |
| D (vehicle) | none | 0 |

Legend: Values are mean ± S.E. of 8 mice per group.
* $P < 0.05$ vs. group A

Dexamethasone and compound G caused a significant reduction (~30%) of neutrophil accumulation. The TAT assays showed that all animals that had received the drug vehicle ip had elevated levels of TAT compared to the untreated controls. This was due to the stress associated with an inflammatory reaction induced by the vehicle and the associated raised endogenous glucocorticoid levels. Dexamethasone caused further elevation of TAT, unlike compound G. This experiment therefore shows that compound G and dexamethasone have an equivalent anti-inflammatory effect when administered at the same dose and that compound G, unlike dexamethasone, does not cause-induction of the gluconeogenic enzyme, tyrosine amino transferase, at this dose. This proves that in-vivo compound G, and thus other compounds in the series shown to have selectivity in the in-vitro assays, will have the desired reduction of side effects that result from transactivation.

One additional interesting observation from this study in the mouse was that compound G did not act as an antagonist towards transactivation. This can be seen because compound G did not reduce the level of TAT compared to the vehicle control groups.

Discussion

Previous investigators have sought to identify selective steroids[44,45]. They have not succeeded in identifying useful compounds. It was thus totally unexpected that we were able to identify a particular series of compounds, as hereinbefore defined in Formula I, II and III, which surprisingly have the desired functionality and, in particular, to identify a Compound (Compound G) with a very considerable degree of selectivity. As the above data demonstrates, examples of compounds according to invention are identified as Compounds A, G, H, I, K, M, N, S and T, the structures of which shown in FIG. 2A, and comparative examples of compounds that fall outside the scope of the present invention are identified as Compounds D, J, L, O, P, Q and S, the structures of which are also shown in FIG. 2A.

The selected series of dexamethasone analogues of the present invention having a structure according Formula I, II, III and IV as defined hereinbefore exhibit selectivity for transrepression over translocation. The selected series of compounds of the present invention clearly bind to the glucocorticoid receptor and do not cause transactivation or cause significantly less transactivation than dexamethasone at concentrations which inhibit the inflammatory process. This is classically a situation where one would expect to see an antagonist activity. This is surprisingly not evident. From a clinical stand point this is of considerable importance as an antagonist to transactivation would counteract the effects of endogenous steroids and induce a state equivalent to a lack of steroid known as Addison's Disease which is characterised by reduced blood pressure, hypokalaemia; coma, reduced resistance to stress and infection.

Thus from the above described experiments, the selected series of dexamethasone analogues according Formula I, II and III as defined hereinbefore have been shown to have the characteristics necessary for a selective steroid receptor agonist with reduced side effects, namely the defined compounds:

1. Cause transrepression to the same or a significantly greater extent than dexamethasone and inhibit inflammation as effectively as dexamethasone
2. Do not transactivate at clinically relevant concentrations in the in-vitro assays and in the in-vivo assay also fail to transactivate and hence will not cause the characteristic steroid side-effects that result form this mechanism and which severely limit the utility of these drugs in clinical practice
3. Do not antagonize the effects of endogenous steroids and hence do not have the capacity to induce an Addisonian side-effect picture.
4. Induce apoptosis which is a mechanism important to clonal selection and the treatment of inflammation and transplant rejection and is the basis by which steroids treat haematological and other malignancies.

Thus the particular compounds having a structural formula according to Formula I, II or II as hereinbefore defined, have been shown to have the characteristics of a group of steroids that have the desired therapeutic profile for reduced side effects whilst maintaining efficacy. Other investigators have identified molecules that have some selectivity in in-vitro assays. RU24858 was shown to have 2 fold selectivity for transrepression over transactivation in-vitro. This compound however failed to show the desired profile in-vivo[44,45]. Compound G was shown to have the desired profile in vivo and this is almost certainly due to the fact that it shows great selectivity (approximately 1000 fold in vitro), is highly potent for transrepression and because it fails to induce a maximal transactivation even at very high concentrations.

EXAMPLE 9

Synthesis of the Novel Compounds According to Formula III and IV

One skilled in the art will appreciate that the following process may be used in order to synthesize the novel compounds according to Formula III and IV from Compound G

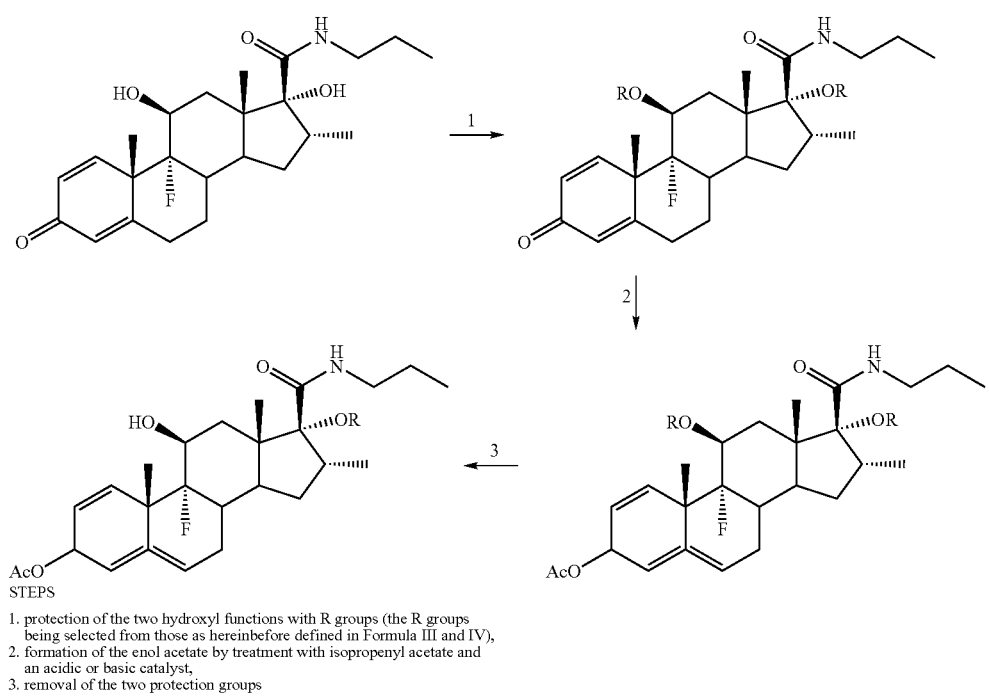

STEPS
1. protection of the two hydroxyl functions with R groups (the R groups being selected from those as hereinbefore defined in Formula III and IV),
2. formation of the enol acetate by treatment with isopropenyl acetate and an acidic or basic catalyst,
3. removal of the two protection groups

REFERENCE LIST

1. Pallardy M, Biola A. [Induction of apoptosis in lymphocytes by glucocorticoids: between physiology and pharmacology]. *C.R. Seances Soc. Biol. Fil.* 1998; 192:1051-63.
2. Cato A C, Wade E. Molecular mechanisms of anti-inflammatory action of glucocorticoids. *Bioessays* 1996; 18:371-8.
3. McColl K S, He H, Zhong H, Whitacre C M, Berger N A, Distelhorst C W. Apoptosis induction by the glucocorticoid hormone dexamethasone and the calcium-ATPase inhibitor thapsigargin involves Bc1-2 regulated caspase activation. *Mol. Cell Endocrinol.* 1998; 139:229-38.
4. Miyashita T, Nagao K, Krajewski S, Salvesen G S, Reed J C, Inoue T et al. Investigation of glucocorticoid-induced apoptotic pathway: processing of caspase-6 but not caspase-3. *Cell Death. Differ.* 1998; 5:1034-41.
5. Reichardt H M, Kaestner K H, Tuckermann J, Kretz O, Wessely O, Bock R et al. DNA binding of the glucocorticoid receptor is not essential for survival [see comments]. *Cell* 1998; 93:531-41.
6. Ray D W, Gibson S, Crosby S R, Davies D, Davis J R, White A. Elevated levels of adrenocorticotropin (ACTH) precursors in post-adrenalectomy Cushing's disease and their regulation by glucocorticoids. *J. Clin. Endocinol. Metab.* 1995; 80:2430-6.
7. Ray D W, Davis J R, White A, Clark A J. Glucocorticoid receptor structure and function in glucocorticoid-resistant small cell lung carcinoma cells. *Cancer Res.* 1996; 56:3276-80.
8. Ray D W, Suen C-S, Brass A, Soden J, and White A. Structure/function of the human glucocorticoid receptor: tyrosine 735 is important for transactivation. Mol. Endocrinol, 13, 1855-1864. 1999. Ref Type: Generic
9. Riccardi C, Zollo O, Nocentini G, Bruscoli S, Bartoli A, D'Adamio F et al. Glucocorticoid hormones in the regulation of cell death. *Therapie* 2000; 55; 165-9.
10. Cifone M G, Migliorati G, Parroni R, Marchetti C, Millimaggi D, Santoni A et al., Dexamethasone-induced thymocyte apoptosis: apoptotic signal involves the sequential activation of phosphoinositide-specific phospholipase C, acidic sphingomyelinase, and caspases. *Blood* 1999; 93:2282-96.
11. Messmer U K, Winkel G, Briner V A, Pfeilschifter J. Glucocorticoids potently block tumour necrosis factor-a. *Br. J. Pharmacol.* 1999; 127:1633-40.
12. Schmidt M, Pauels H G, Lugering N, Lugering A, Domschke W, Kucharzik T. Glucocorticoids induce apoptosis in human monocytes: potential role of IL-1 beta. *J. Immunol.* 1999; 163:3484-90.
13. Yang Y, Ashwell J D. Thymocyte apoptosis. *J. Clin. Immunol.* 1999; 19:337-49.
14. Ashwell J D, King L B, Vacchio M S. Cross-talk between the T cell antigen receptor and the glucocorticoid receptor regulates thymocyte development. *Stem Cells* 1996; 14:490-500.
15. Brannigan A E, O'Connell P R, Hurley H, O'Neill A, Brady H R, Fitzpatrick J M et al. Neutrophil apoptosis is delayed in patients with inflammatory bowel disease. *Shock* 2000; 13:361-6.
16. Horwitz K B, Jackson T A, Bain D L, Richer J K, Takimoto G S, Tung L. Nuclear receptor coactivators and corepressors. *Mol. Endocninol.* 1996; 10:1167-77.
17. Perlmann T, Evans R M. Nuclear receptors in Sicily: all in the famiglia. *Cell* 1997; 90:391-7.
18. Evans R M, Hollenberg S M. Cooperative and positional independent trans-activation domains of the human glucocorticoid receptor. *Cold Spring Harb. Symp. Quant. Biol.* 1988; 63 Pt 2:813-8.
19. Kamei Y, Xu L, Heinzel T, Torchia J, Kurokawa R, Gloss B et al. A CBP integrator complex mediates transcriptional activation and AP-1 inhibition by nuclear receptors. *Cell* 1996; 85:403-14.
20. Hong H, Darimont B D, Ma H, Yang L, Yamamoto K R, Stallcup M R. An additional region of coactivator GRIP1 required for interaction with the hormone-binding domains of a subset of nuclear receptors. *J. Biol. Chem.* 1999; 274:3496-502.
21. Chen H, Lin R J, Schiltz R L, Chakravarti D, Nash A, Nagy L et al. Nuclear receptor coactivator ACTR is a novel histone acetyltransferase and forms a multimeric activation complex with P/CAF and CBP/p300. *Cell* 1997; 90:569-80.
22. Chen J D, Evans R M. A transcriptional co-repressor that interacts with nuclear hormone receptors [see comments]. *Nature* 1995; 377:454-7.
23. Schule R, Evans R M. Functional antagonism between oncoprotein c-Jun and steroid hormone receptors. *Cold Spring Harb. Symp. Quant. Biol.* 1991; 56:119-27.
24. Miner J N, Yamamoto K R. Regulatory crosstalk at composite response elements. *Trends. Biochem. Sci.* 1991; 16:423-6.
25. Heck S, Kullmann M, Gast A, Ponta H, Rahmsdorf H J, Herrlich P et al. A distinct modulating domain in glucocorticoid receptor monomers in the repression of activity of the transcription factor AP-1. *EMBO J.* 1994; 13:4087-95.
26. Wade E J, Heck S, Cato A C. Glucocorticoid receptor-activator protein-I interactions in drug design. *Biochem. Soc. Trans.* 1995; 23:946-52.
27. Konig H, Ponta H, Rahmsdorf H J, Herlich P. Interference between pathway-specific transcription factors: glucocorticoids antagonize phorbol ester-induced AP-1 activity without altering AP-1 site occupation in vivo. *EMBO J.* 1992; 11:2241-6.
28. Caldenhoven E, Liden J, Wissink S, van-de S A, Raaijmakers J, Koenderman L et al. Negative cross-talk between RelA and the glucocorticoid receptor: a possible mechanism for the antiinflammatory action of glucocorticoids. *Mol. Endocrinol.* 1995; 9:401-12.
29. Ray A, Prefontaine K E. Physical association and functional antagonism between the p65 subunit of transcription factor NF-kappa B and the glucocorticoid receptor. *Proc. Natl. Acad. Sci. U.S.A.* 1994; 91:752-6.
30. Scheinman R I, Cogswell P C, Lofquist A K, Baldwin-AS J. Role of transcriptional activation of I kappa B alpha in mediation of immunosuppression by glucocorticoids [see comments]. *Science* 1995; 270:283-6.
31. Scheinman R I, Gualberto A, Jewell C M, Cidlowski J A, Baldwin-AS J. Characterization of mechanisms involved in transrepression of NF-kappa B by activated glucocorticoid receptors. *Mol. Cell Biol.* 1995; 15:943-53.
32. Heck S, Bender K, Kullmann M, Gottlicher M, Herriich P, Cato A C. I kappaB alpha-independent downregulation of NF-kappaB activity by glucocorticoid receptor. *EMBO J.* 1997; 16:4698-707.
33. Cato A C, Wade E. Molecular mechanisms of anti-inflammatory action of glucocorticoids. *Bioessays* 1996; 18:371-8.
34. Jonat C, Rahmsdorf H J, Park K K, Cato A C, Gebel S, Ponta H et al. Antitumor promotion and antiinflammation: down-modulation of AP-1 (Fos/Jun) activity by glucocorticoid hormone. *Cell* 1990; 62:1189-204.

35. Kam J C, Szefler S J, Surs W, Sher E R, Leung D Y. Combination IL-2 and IL-4 reduces glucacorticoid receptor-binding affinity and T cell response to glucocorticoids. *J. Immunol.* 1993; 151:3460-6.
36. Sher E R, Leung D Y, Surs W, Kam J C, Zieg G, Kamada A K et al. Steroid-resistant asthma. Cellular mechanisms contributing to inadequate response to glucocorticoid therapy. *J. Clin. Invest.* 1994; 93:33-9.
37. Barnes Pd. Anti-inflammatory actions of glucocorticoids: molecular mechanisms [editorial]. *Clin. Sci. Coich.* 1998; 94:557-72.
38. Vayssiere B M, Dupont S, Choquart A, Petit F, Garcia T, Marchandeau C et al. Synthetic glucocorticoids that dissociate transactivation and AP-1 transrepression exhibit anti-inflammatory activity in vivo. *Mol. Endocrinol.* 1997; 11:1245-55.
39. Vanden Berghe W, Francesconi E, De Bosscher K, Resche-Rigon M, Haegeman G. Dissociated glucocorticoids with anti-inflammatory potential repress interleukin-6 gene expression by a nuclear factor-kappaB-dependent mechanism. *Mol. Pharmacol.* 1999; 56:797-806.
40. Hofmann T G, Hehner S P, Bacher S, Droge W, Schmitz M L. Various glucocorticoids differ in their ability to induce gene expression, apoptosis and to repress NF-kappaB-dependent transcription. *FEBS Lett.* 1998; 441:441-6.
41. Wurtz J M, Bourguet W, Renaud J P, Vivat V, Chambon P, Moras D et al. A canonical structure for the ligand-binding domain of nuclear receptors [see comments] [published erratum appears in Nat Struct Biol 1996 February; 3(2): 206]. *Nat. Struct. Biol.* 1996; 3:87-94.
42. Sippl, M. J. Boltzmann's principal, knowledge based mean fields and protein folding. An approach to the computational determinaton of protein structures. Journal of Computer Aided Molecular Design 7, 473-501. 1993. Ref Type: Generic
43. Vanden Berghe W, Francesconi E, De Bosscher K, Resche-Rigon M, Haegeman G. Dissociated glucocorticoids with anti-inflammatory potential repress interleukin-6 gene expression by a nuclear factor-kappaB-dependent mechanism. *Mol. Pharmacol.* 1999; 56:797-806.
44. Belvisi M G, Brown T J, Wicks S, Foster M L. New Glucocorticosteroids with an improved therapeutic ratio? *Pulm. Pharmacol. Ther.* 2001; 14:221-7.
45. Belvisi M G, Wicks S L, Battram C H, Bottoms S E, Redford J E, Woodman P et al. Therapeutic benefit of a dissociated glucocorticoid and the relevance of in vitro separation of transrepression from transactivation activity. *J. Immunol.* 2001; 166:1975-82.

The invention claimed is:

1. A pharmaceutical composition which comprises a compound according to Formula I and a pharmaceutically acceptable carrier:

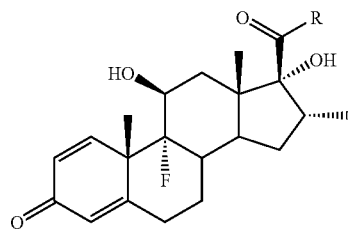

FORMULA I wherein R is $H_2C-O-C(O)-NHR^3$ and $R^3$ is selected from a benzyl or a substituted benzyl group.

2. The pharmaceutical composition of claim 1 wherein the substituted benzyl group is a halobenzyl group.

3. The pharmaceutical composition of claim 2 wherein the halobenzyl group is a fluorobenzyl.

4. A pharmaceutical composition which comprises a compound selected from the following:

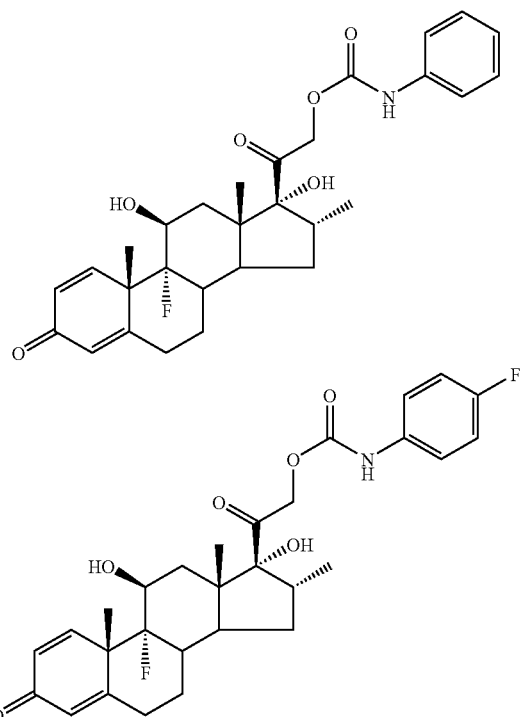

and a pharmaceutically acceptable carrier.

* * * * *